United States Patent [19]
Atkinson et al.

[11] Patent Number: 5,772,996
[45] Date of Patent: Jun. 30, 1998

[54] **PHARMACEUTICAL COMPOSITIONS CONTAINING SUPEROXIDE DISMUTASE FROM *BACILLUS STEAROTHERMOPHILUS* AND *BACILLUS CALDOTENAX***

[75] Inventors: Anthony Atkinson; Kevin John Bown; John Karl Brehm; Stephen Phillip Chambers; Nigel Peter Minton, all of London, England

[73] Assignee: Public Health Laboratory Service Board, London, United Kingdom

[21] Appl. No.: 445,909

[22] Filed: May 22, 1995

Related U.S. Application Data

[63] Continuation of Ser. No. 978,697, filed as PCT/GB91/01325, Aug. 2, 1991, published as WO92/02625, Feb. 20, 1992, abandoned.

[30]     Foreign Application Priority Data

Aug. 3, 1990 [GB]    United Kingdom ................... 9017037

[51] Int. Cl.⁶ ............................ A61K 38/44; C12N 9/08; C12N 15/63
[52] U.S. Cl. ....................... 424/94.4; 435/192; 435/252.5
[58] Field of Search ................................ 435/192, 252.5; 424/94.4

[56]              References Cited

U.S. PATENT DOCUMENTS

| | | | |
|---|---|---|---|
| 4,385,120 | 5/1983 | Atkinson et al. | 435/194 |
| 4,563,349 | 1/1986 | Miyata et al. | 424/94.4 |
| 4,820,642 | 4/1989 | Edman et al. | 435/252.33 |
| 4,952,409 | 8/1990 | Bando et al. | 424/450 |
| 4,957,740 | 9/1990 | Wilder | 424/94.4 |
| 5,080,886 | 1/1992 | Mickle et al. | 424/94.4 |
| 5,091,180 | 2/1992 | Walker et al. | 424/94.4 |

FOREIGN PATENT DOCUMENTS

| | | |
|---|---|---|
| 0172577 | 2/1986 | European Pat. Off. . |
| 0289667 | 11/1988 | European Pat. Off. . |
| 0314274 | 5/1989 | European Pat. Off. . |
| 63-245671 | 10/1988 | Japan . |
| 1196294 | 8/1989 | Japan . |
| 2183658 | 6/1987 | United Kingdom . |
| 89/01033 | 2/1989 | WIPO . |

OTHER PUBLICATIONS

Bowie et al., 247 Science 1306–10, 1306 (1990).
Jones et al., 25 Biochemistry 1887–91 (1986).
Brock et al., 107 J. Mol. Biol. 175–78 (1976).
Beck et al., 6 Biotechnology 930–35 (1988).

Ravindranath et al. Isolation and characterization of a manganese–containing superoxide dismutase from yeast. The Journal of Biological Chemistry. vol. 250, No. 15, pp. 6107–6112, Aug. 10, 1975.

Windholz et al, *The Merck Index*, p. 1092, Monograph 7441, (1983).

Parker et al "Iron– and Manganese–Containing Superoxide Dismutases . . . " *FEBS Lett.* 229(2): 377–382 (Mar. 1988).

Parker et al "Crystal Structure of Manganese Superoxide Dismutase from *Bacillus stearothermophilus* . . . " *J. Mol. Biol.* 199: 649–661 (1988).

Schulz et al *Principles of Protein Structure*, pp. 14–16 (1979).

Bowler et al, "Characterization of the *Bacillus stearothemophilus* Manganese Superoxide Dismutase Gene . . . ", J. Bacter. 172(3): 1539–1546 (Mar. 1990).

Brock et al "Superoxide Dismutase from *Bacillus stearothermophilus* . . . " *Biochem.* 19: 2873–2882 (Jun. 1980).

Yousten et al "A Single Form of Superoxide Dismutase Found in *Bacillus popilliae* . . . ", *J. Gen. Appl. Microbiol.* 22: 161–164 (1976).

Tsukuda et al, "Isolation of Manganese–Containing Superoxide Dismutase from *Bacillus subtilis* . . . ", *Agric. Biol. Chem.* 47(12): 2865–2870 (1983).

*Primary Examiner*—Elizabeth C. Kemmerer
*Assistant Examiner*—Brian Lathrop
*Attorney, Agent, or Firm*—Kirschstein, et al.

[57]                ABSTRACT

A pharmaceutical composition for use in the prophylaxis or treatment of pathological conditions resulting from the presence of superoxide radicals, comprising a manganese-superoxide dismutase (MnSOD) enzyme and a pharmaceutically acceptable excipient. The MnSOD enzyme is in native form and has substantially the amino acid sequence of SEQ ID NO: 17 or SEQ ID NO: 29 and is free of pyrogens consisting of macromolecular substances native to *Bacillus Stearothermophilus* (BS) or *Bacillus Caldotenax* (BC). Processes for producing the novel pharmaceutical composition and a method for the prophylaxis or treatment of pathological conditions resulting from the presence of superoxide radicals utilizing the novel composition are also disclosed.

12 Claims, 15 Drawing Sheets

Fig.1.

```
      H    I    D    K    E    T    M    N    I    H
---  CAC  ATC  GAC  AAA  GAA  ACG  ATG  AAC  ATT  CAC
     |||  |||  |||  |||  |||  |||  |||  |||  ||:  |||
3'-  GTG  TAG  CTG  TTT  CTT  TGC  TAC  TTG  TAG  GTG

H    T    K    H    H    N    T    -       aa sequence

CAC  ACG  AAG  CAC  CAT  AAC  AC   ---     nt sequence
     |||  |||  ||:  |||  ||:  |||  ||
     GTG  TGC  TTT  GTG  GTG  TTG  TG - 5'      probe
```

HindIII
AAGCTTTTCCACAGCTGGACGAATACGTTCATCGCAGACACCTTTCTTTATCTCCTTTCCATTGTAGCCGGGAAAGA    80

GGAAGAATTCAACTTGAGACAAAGAAAAGCGGGCATCTTCCCGCTTTAGTCAGAAGGCAAATGAAAGGTTTCAAGCAAG    160

GCGCGGCCATTGCAACACCCGTTCATTTAGTGCATCGGCTTCGGAACGAATGGCAGCCATATACTATAGCTTGTCATTATG    240

AAGAAACGGTCAACGGTGTGTTGAAAATATGTAAACAAAAACCGAGGACAAGTCGATTGAAACATTGTGCCAACTT    320

TGGTAAGCTAATCTCAAGCGAACGCTTTGGCGTTCGTGTACATAAATCAAAAAGGAGGATCGGTATGCCATTGAATT    400
                                       S.D.                    MetProPheGluLe
                                                                     ORF A

GCCAGCATTGCCGTATCCGTATGATGCTCTGGAGCCGCACATCGACAAAGAAACATTCACCACGAAGCACC    480
uProAlaLeuProTyrProTyrAspAlaLeuGluProHisIleAspLysGluThrMetAsnIleHisThrLysHisH

ATAACACATACGTTACAAATTTGAATGCGGCCTTGAAGGACATCCGGATTTGCAAAACAAATGCTCGAAGAACTGCTC    560
isAsnThrTyrValThrAsnLeuAsnAlaAlaLeuLysGluGlyHisProAspLeuGlnAsnLysSerLeuGluLeuLeu

AGCAATTTGGAAGCCCTTCCGGAAAGCATCCGACGGTGCCGCAACGGCGGCCATGCGAACCACTGCTTT    640
SerAsnLeuGluAlaLeuProGluSerIleArgThrAlaValArgAsnAsnGlyGlyHisAlaAsnHisSerLeuPh

CTGGACGATTTGTCGCCAAATGGCGGGCCGAGCCGACGGGTGAGCCGCCATCAACAAAAATTCGGCAGCT    720
eTrpThrIleLeuSerProAsnGlyGlyGluProThrGlyGluLeuAlaAspAlaIleAsnLysPheGlySerP

Fig.3A

```
TCACCGCGTTCAAAGACGAGTTTTCGAAAGCAGCGGGCCGGTTTCCGGTTGGGCCATGGCTTGTTGTGAACAAC     800
heThrAlaPheLysAspGluPheSerLysAlaAlaAlaGlyArgPheGlySerGlyTrpAlaTrpLeuValAsnAsn

GGGGAGCTGGAAATCACAAGCACGCCGAACCAAGATTCGCCGATTATGGAAGGCAAAACGCCGATTCTCGGCTTGGACGT     880
GlyGluLeuGluIleThrSerThrProAsnGlnAspSerProIleMetGluGlyLysThrProIleLeuGlyLeuAspVa

TTGGGAGCATGCGTACTACTTGAAATACCAAAACCGCGTCCGGAATACATTGCCGCATTCTGGAACGTCGTCAACTGGG     960
lTrpGluHisAlaTyrTyrLeuLysTyrGlnAsnArgArgProGluTyrIleAlaAlaPheTrpAsnValValAsnTrpA

ACGAAGTGGCGAAACGGTACAGCGAAGCGAAAGCAAATAATGAACAAAGCGGGGGAAACACAACGCTCCGCTTTTTT     1040
spGluValAlaLysArgTyrSerGluAlaLysTer

TCGACGAAGGGGCAGGCAAAGGAGCGGTTTCGTTGCGCCGGTGCATAGAGGCGGCAGAAATGGCCACTACCCGA     1120

TAGATGAAAAGGGGAGTTTGCAATGGCATTTTTCCAAAACTAACCGGCCAAGAACAAGTGAACGGCGACCTGTTGCTTT     1200
                MetAlaPhePheGlnLysLeuThrGlyGlnGluGlnValAsnArgAspLeuLeuLeuL
                ORF B

TGCTTTGCATCGGCGGGTTTACGCGCTCGGCGTGTTCCCGTGTCGAACACGTTTGTCAACATTATTGTGAAACAGACC     1280
euLeuCysIleGlyGlyPheTyrAlaLeuGlyValSerLeuSerAsnThrPheValAsnIleTyrLeuTrpLysGlnThr
            NruI

GGCGATTTCGCGA     1294
GlyAspPheArgGlu
```

Fig. 3B

```
                                                          AccI
                                                          SalI                                    XhoI
            SmaI                                                       AatII MluI  NcoI BglII  Stu
     EcoRI SstI KpnI  BamHI      XbaI                                                          
ATGACCATGATTACGAATTCGAGCTCGGTACCCGGGGATCCTCTAGAGTCGACGTCACGCGTCCATGGAGATCTCGAGGC
 M  T  M  I  T

AccI
                                                                                 SalI
         HindIII SphI PstI StuI      BglII NcoI MluI AatII         XbaI BamHI
ATGACCATGATTACGAATTCGAGCTCGCATGCCTGCAGGCCTCGAGATCTCCATGGACGCGTGACGTCGACTCTAGAGGATCC
 M  T  M  I  T AccI
                                                    SalI
              NaeI EcoRV BamHI      AatII MluI PstI HindIII EcoRI SstI     XbaI
ATGACCATGATTACGAATTGCCGGCGATATCGGATCCATATGACGTCGACGCGTCTGCAGAAGCTTCTAGAATTCGAGCT
 M  T  M  I  T
                                              NdeI KpnI
        XhoI                                                                 SmaI SstI EcoRI Hi
     NruI StuI  BglII ClaI SphI NcoI      AatII MluI NcoI BglII       XhoI
ATGACCATGATTACGCCAAGCTCGCGAGGCCTCGAGATCTATCGATGCATGCCATGGTACCCGGGAGCTCGAATTCTAGA
 M  T  M  I  T AccI
                                                                  SalI
            SmaI                                AatII MluI NcoI BglII   Stu
     EcoRI SstI KpnI  BamHI XbaI                                      XhoI
ATGACCATGATTACGAATTCGAGCTCGGTACCCGGGGATCCTCTAGAGTCGACGTCACGCGTCCATGGAGATCTCGAGGCC
 M  T  M  I  T AccI
                                                                          SalI
         HindIII SphI PstI      XhoI      NcoI MluI AatII              XbaI BamHI
ATGACCATGATTACGAAGCTTGCATGCCTGCAGGCCTCGAGATCTCCATGGACGTCGACGTCGACTCTAGAGGATCC
 M  T  M  I  T AccI
                             SalI
      XbaI          PstI MluI    AatII             NdeI
     EcoRI HindIII                    BamHI  EcoRV NaeI         SstI
ATGACCATGATTACGAATTCTAGAAGCTTCTGCAGACGCGTCGACGTCATATGGATCCGATATCGCCGGCAATTCGAGCT
 M  T  M  I  T XhoI
     NruI StuI BglII SmaI BamHI EcoRV BclI  HpaI  BglII EcoRI
ATGACCATGATTACGCCAAGCTCGCGAGGCCTCCCGGGATCCGATATCTGATCAGTTAACAGATCTGAATTC
 M  T  M  I  T
```

Fig.6A

```
                                                                                                                                                  pMTL25
                                                                                                                  - pMTL24

- pMTL23                                         CACTGGCC
                                                           - pMTL22                                                                   L  A
                                                                                                                  CACTGGCC
                                                                                     CACTGGCC                     L  A
                                              CACTGGCC                               L  A
                                              L  A

I  PstI  SphI  HindIII
        CTGCAGGCATGCAAGCTTGGCACTGGCC  - pMTL20
                                L  A SmaI
            KpnI  SstI  EcoRI
        CCGGGTACCGAGCTCGAATTCACTGGCC  - pMTL21
                                L  A
                            AccI
                            SalI
              KpnI            Xho I
        SmaI  NcoI  SphI  ClaI  BglII  StuI  NruI
        CCCGGGTACCATGGCATGCAAGATCGATAGATCTCGAGGCCTCGCGAGCTTGGCACTGGCC
                                                                L  A
                                   AccI
                                   SalI  NdeI
        ndIII PstI  MluI  AatII  BamHI EcoRV NaeI
        AGCTTCTGCAGACGCGTCGACGTCATATGGATCCGATATCGCCGGCAATTCACTGGCC
                                                          L  A PstI  SphI  HindIII    AccI                      SmaI
                                   SalI  XbaI  BamHI  KpnI  SstI  EcoRI
        TGCAGGCATGCAAGCTTGCATGCCTCGAGGTCGACTCTAGAGGATCCCGGGTACCGAGCTCGAATTCACTGGCC
                                                                            L  A SmaI
            KpnI  SstI  EcoRI      AccI
                            SalI         BamHI XbaI   SalI   PstI  SphI  HindIII
        CCGGGTACCGAGCTCGAATTCGGGTACCCGGGATCCTCTAGAGTCGACCTGCAGGCATGCAAGCTTGGCACTGGCC
                                                                              L  A KpnI            XhoI
        SmaI  NcoI  SphI  ClaI  BglII  StuI  NruI
        CCCGGGTACCATGGCATGCAAGATCGATAGATCTCGAGGCCTCGCGAGCTTGGCACTGGCC  -pMTL26
                                                             L  A
                            AccI
                            SalI  NdeI
        HindIII PstI  MluI  AatII   BamHI EcoRV NaeI
        TAGAAGCTTCTGCAGACGCGTCGACGTCATATGGATCCGATATCGCCGGCAATTCACTGGCC  - pMTL28
                                                                  L  A
```

```
                S.D.
TGTACATAAATCAAAAAGGAGGAGATCGGTATGCCATTTGAATTGCCAGCATTGCCGTAT   60
                           MetProPheGluLeuProAlaLeuProTyr t  g
CCGTATGATGCGCTTGAGCCGCACATCGACAAAGAAACGATGAACATTCACCACACGAAG  120
ProTyrAspAlaLeuGluProHisIleAspLysGluThrMetAsnIleHisHisThrLys

CACCATAACACATACGTTACAAATTTGAATGCGGCGCTTGAAGGGCATCCGGATTTGCAA  180
HisHisAsnThrTyrValThrAsnLeuAsnAlaAlaLeuGluGlyHisProAspLeuGln c                                    c
AACAAATCGCTCGAAGAATTGCTCAGCAATTTGGAAGCCCTTCCGGAAAGCATTCGCACG  240
AsnLysSerLeuGluGluLeuLeuSerAsnLeuGluAlaLeuProGluSerIleArgThr c            g
GCGGTGCGCAACAACGGCGGCGGTCATGCAAACCACTCGCTTTTCTGGACGATTTTGTCG  300
AlaValArgAsnAsnGlyGlyGlyHisAlaAsnHisSerLeuPheTrpThrIleLeuSer c                      c   c
CCAAATGGCGGCGGTGAGCCGACGGGTGAGCTGGCTGAGGCGATCAACAAAAAATTCGGC  360
ProAsnGlyGlyGlyGluProThrGlyGluLeuAlaGluAlaIleAsnLysLysPheGly
                                           Asp
              c                                        c   t
AGCTTCACCGCGTTTAAAGACGAGTTTTCGAAAGCAGCGGCCGGCCGTTTCGGTTCTGGC  420
SerPheThrAlaPheLysAspGluPheSerLysAlaAlaAlaGlyArgPheGlySerGly t                   c   a                       t
TGGGCATGGCTTGTCGTGAACAACGGCGAGCTGGAAATTACGAGCACGCCGAACCAAGAC  480
TrpAlaTrpLeuValValAsnAsnGlyGluLeuGluIleThrSerThrProAsnGlnAsp t
TCGCCGATCATGGAAGGCAAAACGCCGATTCTCGGCTTGGACGTTTGGGAGCATGCGTAC  540
SerProIleMetGluGlyLysThrProIleLeuGlyLeuAspValTrpGluHisAlaTyr g  c
TACTTGAAATACCAAAACCGCCGTCCGGAATACATTGCCGCATTCTGGAACATTGTCAAC  600
TyrLeuLysTyrGlnAsnArgArgProGluTyrIleAlaAlaPheTrpAsnIleValAsn
                                                         Val
                                        a  a       g
TGGGACGAAGTGGCGAAACGGTACAGCGAAGCGAAAGCGAAGTAATCAACAAAGCGGGGC  660
TrpAspGluValAlaLysArgTyrSerGluAlaLysAlaLysTer

→     c ← t          t-     a         g             g          g
GAAACAAAACGCCCCGCTTTTTTTAGCGACGGAGGGTGCAGGCAAAGGAAGCGGTTTTCT  720
terminator t               g  a                          c
TCGCGCCGGGTGCATAGAGGCTGCGGAAATGGCCACACTACCGGATAGATGAAAAGGGGA  780
```

PHARMACEUTICAL COMPOSITIONS CONTAINING SUPEROXIDE DISMUTASE FROM *BACILLUS STEAROTHERMOPHILUS* AND *BACILLUS CALDOTENAX*

CROSS-REFERENCE TO RELATED APPLICATIONS

This application is a continuation of U.S. Ser. No. 07/978,697, filed Feb. 2, 1993, now abandoned, which is a national stage application of PCT/GB91/01325, filed Aug. 2, 1991 under 35 U.S.C. §371, published as WO92/02625 Feb. 20, 1992.

BACKGROUND OF THE INVENTION

1. Field of the Invention

This invention relates to a process for producing enzymes having superoxide dismutase activity, novel superoxide dismutase enzymes and novel pharmaceutical compositions comprising enzymes having superoxide dismutase activity.

2. Description of Related Art

One consequence of oxidative metabolism is the generation of superoxide radicals ($O_2^-$) which mediate extensive damage to the cellular components of living organisms. The molecular dismutation of $O_2^-$ to hydrogen peroxide ($H_2O_2$) and oxygen ($O_2$) is catalysed by a ubiquitous class of metalloenzymes termed superoxide dismutases (SODs). Other abbreviations appear in the appendix preceding the figure legends. The prevalence of SODs in all living organisms which tolerate exposure to molecular $O_2$ has led to the compelling suggestion that these enzymes form the first line of the cell's defence against oxygen damage (Fridovich, 1975).

On the basis of their metal ion content, three classes of SOD are recognised: Cu/Zn—, Fe—, and Mn-containing enzymes. While all three forms catalyse the same reaction, the Fe-containing SODs (FeSOD) are largely confined to prokaryotes and the Cu/Zn enzymes (Cu/ZnSOD) predominantly to eukaryotes. Mn-containing SODs (MnSOD) are universally present. In eukaryotes MnSODs are localised to the mitochondria, while the Cu/ZnSODs reside in the cytosol (Geller and Winge, 1984). *Escherichia coli* contains three isoenzymatic forms of SOD: a MnSOD (sodA), a FeSOD (sodB) and a hybrid enzyme containing both manganese and iron (Hassan and Fridovich, 1977).

SODs from various sources are currently of great interest as potential therapeutic treatments for oxidative damage. Their use in a clinical setting for the treatment of a wide variety of disorders has been proposed (see Beck et al., 1988).

These include: (i) prevention of oncogenesis, tumour promotion and invasiveness, and UV-induced damage; (ii) protection of cardiac tissue against post-ischemia reperfusion damage; (iii) as an antiinflamatory agent; (iv) to reduce the cytotoxic and cardiotoxic effects of anticancer drugs, and; (v) to improve the longevity of living cells. Indeed, currently bovine Cu/ZnSOD is being utilised for the treatment of inflamed tendons in horses and for treating osteoarthritis in man (Puhl et al., 1984).

SODs currently proposed for therapy suffer the severe disadvantage of being highly immunogenic and consequently, as a result of the antibody response produced on administration, have proved to be of low clinical utility. Further available SODs, particularly those from mammalian sources, are difficult to obtain in large amounts in view of their low concentration in mammalian cells and the tedious isolation procedures required to produce them in satisfactory levels of purity.

Thus for example EP-A-O 172 577 (Takeda) describes the pharmaceutical use of the MnSOD of *Serratia marcescens* as an antiinflammatory agent, but the only dosage forms described are enteric capsules and tablets. Similarly JP-A-63245671 (Shobo K. K. and Unichika K. K.) suggests the pharmaceutical use of a modified MnSOD of *Bacillus stearothermophilus* in the cosmetic and pharmaceutical fields. The unmodified enzyme is stated to be unsuitable for use due to its antigenicity and the specification prescribes a modification using a polyalkylene glycol.

GB-A-2183658 describes the expression of human MnSOD in *E.coli* and proposes various pharmacological uses for the resulting product. Also the pharmaceutical use of the SOD of *Streptococcus lactis* is described in EP-A-0 289 667.

Available SOD enzymes suffer disadvantages limiting their clinical utility, including a relatively short half-life in solution, loss of activity at pHs below pH7 and high antigenicity. Hitherto it has consequently not been possible to produce effective pharmaceutical compositions for countering the adverse effects associated with the presence in tissues of superoxide radicals.

It has now been surprisingly found that the MnSOD enzymes of *B.stearothermophilus* (BS) and *B.caldotenax* (BC) when in native, i.e. chemically unmodified form, have a significantly lower antigenicity than those derived from eukaryotic cells and can be used with greater therapeutic effect.

Contrary to the teaching of JP-A-63245671 the BS and BC MnSOD enzymes used for producing pharmaceutical compositions according to the invention have been found to be essentially non-antigenic in native form. The suggestion in JP-A-63245671 that BS MnSOD is highly antigenic may be a result of the highly impure nature of the enzyme used in the described procedures. According to our findings, both the BS and BC enzyme, either when subjected to purification procedures so as to remove pyrogenic impurities associated with cell components of the BS and BC organisms, or if produced by recombinant techniques which necessarily avoid the presence of such impurities, are essentially non-antigenic (to the limits of available immunoassay techniques).

SUMMARY OF THE INVENTION

Thus according to one aspect of the invention, there are provided pharmaceutical compositions for use in the prophylaxis and/or treatment of pathological conditions resulting from the presence of superoxide radicals, comprising an MnSOD enzyme and a pharmaceutically acceptable excipient, characterised in that the MnSOD enzyme is in native form and has substantially the amino acid sequence of BS or BC MnSOD (SEQ ID NO: 17 or SEQ ID NO: 29).

Preferably the MnSOD enzyme is obtained in native-form by (a) culturing an MnSOD enzyme-producing microorganism so as to produce an MnSOD enzyme-containing culture (b) isolating MnSOD enzyme from the culture, and (c) purifying the isolated MnSOD enzyme so as to produce purified enzyme which is essentially unmodified, chemically, compared to the MnSOD enzyme present in the MnSOD-containing culture produced in step (a).

The culture medium is desirably supplemented with manganese. In order to achieve high levels of expression of MnSOD>0.01 mM manganese is generally required. Thus to obtain levels of expression of around 10% MnSOD (expressed as a percentage of total soluble protein), 0.01 mM of manganese salt should be included.

It is preferred that pharmaceutical compositions according to the invention are substantially free of pyrogens consisting of macromolecular substances native to *B stearothermophilus* or *B caldotenax*. This may be achieved for example by producing the MnSOD enzyme by culturing a transformed microorganism being of Et species other than *B stearothermophilus* or *B caldotenax*.

The MnSOD enzymes preferably have an amino acid sequence selected from (i) the amino acid sequence depicted in FIG. 3 (SEQ ID NO: 17) for BS MnSOD, (ii) the amino acid sequence depicted in FIG. 12 (SEQ ID NO: 29) for BC MnSOD, and (iii) amino acid sequences which differ from the sequences (i) and (ii) by from 1 to 30 amino acid insertions, deletions and/or substitutions.

Sequences (iii) may for example differ from the sequences (i) and (ii) by from 1 to 20, preferably from 1 to 10 amino acid insertions, deletions and/or substitutions.

Most preferably amino acid sequences (iii) differ from the sequences (i) and (ii) by from 1 to 5, e.g. 1, 2 or 3 amino acid insertions, deletions and/or substitutions.

Pharmaceutical compositions according to, the invention may be prepared in the form (a) of an injectable solution, or (b) a solution suitable for perfusing tissues during surgical or transplantation procedures. Such compositions typically contain from 0.001 to 1.0, preferably from 0.01 to 1.0 mg/l of said MnSOD enzyme, preferably from 0.01 to 1.0 mg/l of said MnSOD enzyme, most preferably from 0.05 to 0.5 mg/l of said MnSOD enzyme.

According to a further aspect of the invention there is provided a process for producing a pharmaceutical composition which comprises the steps of (a) culturing an MnSOD enzyme-producing microorganism so as to produce an MnSOD enzyme-containing culture, (b) isolating MnSOD enzyme from the culture, (c) purifying the isolated MnSOD enzyme so as to produce purified enzyme which is essentially unmodified, chemically, compared to the MnSOD enzyme present in the MnSOD-containing culture produced in step (a), and (d) mixing the chemically unmodified MnSOD enzyme with a pharmaceutically acceptable excipient, characterised in that said MnSOD enzyme has substantially the amino acid sequence of BS or BC MnSOD.

As indicated, it is preferred that the transformed microorganism referred to in step (a) is a transformed microorganism of a species other than *B stearothermophilus* or *B caldotenax*.

Further in accordance with the invention there is provided the use of an MnSOD enzyme in the manufacture of a pharmaceutical composition for the prophylaxis and/or treatment of pathological conditions resulting from the presence of superoxide radicals, characterised in that the MnSOD enzyme is in native form and has substantially the amino acid sequence of BS or BC MnSOD.

BS and BC MnSOD enzymes have been found to be particularly useful in the manufacture of infusing solutions for organs undergoing surgery or transplantation.

Thus a more specific use in accordance with the invention comprises using of an MnSOD enzyme in the manufacture of an infusing solution for organs undergoing surgery or transplantation, especially such organs which are isolated from normal blood supply, the MnSOD enzyme being in native form and having substantially the amino acid sequence of BS or BC MnSOD.

The BC and BS MnSOD enzymes used in accordance with the invention have properties which provide distinct advantages compared to previously used SODs. Particularly (a) Both BS and BC MnSODs have a half life in solution:
of >2 hrs at 60° C.
of >30 mins at 65° C.
at least 10 mins at 70° C.
at least 2 mins at 75° C.
at pH7.5 and an MnSOD protein concentration of 0.5 mg/ml (b) Both BC and BS MnSOD retain at least 10% of their full catalytic activity at pHs below 7 and above pH6.

(c) The antigenicity of both enzymes is so low as to be impossible to quantify. Thus whereas enzymes such as *S.lactis* and *S.marcescens* SODs have antigenicities which can be determined by assessing antibody titres in rabbits, normal protocols fail to elicit any antibody response for native BC or BS MnSODs either when produced by recombinant procedures or extracted from BC or BS, followed by purification to remove pyrogens.

(d) Both BC and BS MnSOD have a half life in sterile solution at pH7.5 and a protein concentration of 0.5 mg/ml of >1 year at 4° C. and >3 months at ambient (15°–20° C.). In 50% glycerol at −20° C. (both enzymes still being in liquid state under these conditions) their half lives are in excess of 5 years.

In addition to the specific pharmacological uses described herein, the BS and BC MnSOD enzymes of the invention may be used industrially as follows:

(i) The generation of hydrogen peroxide in diagnostic assays. Many enzymes and reagents are available for estimating/monitoring hydrogen peroxide.

(ii) Removal of superoxide in industrial systems. Many superoxide scavengers are used in industry including perfumes, anaerobic processing etc.

(iii) Removal of superoxide (a taste destroyer and spoiler) in foods etc.

The MnSOD enzyme of *Bacillus caldotenax* has never been isolated or described hitherto and is a novel substance forming a further aspect of the present invention.

Thus the invention further provides an MnSOD enzyme being in substantially pure form and having essentially the amino acid sequence of *B caldotenax*, said amino acid sequence being selected from (i) the amino acid sequence depicted in FIG. 12 (SEQ ID NO: 24), (ii) amino acid sequences which differ from the sequence (i) by from 1 to 30 amino acid insertions, deletions and/or substitutions, with the proviso that said amino acid sequences (ii) have Glu in the location marked 103 and/or have Ile in the location marked 188.

Sequences (ii) may for example differ from the sequence (i) by from 1 to 20, preferably from 1 to 10 amino acid insertions, deletions and/or substitutions.

To date the structural genes encoding various SODs have been cloned from a number of different eukaryotic and prokaryotic sources, including the Cu/ZnSODs of man (Sherman et al., 1983), *Saccharomyces cerevisiae* (Bermingham et al., 1988), and Drosophila (Seto et al., 1989), the human MnSOD (McCord et al., 1977), the FeSOD of *Anacystis nidulans* (Laudenbach et al., 1989), and the MnSOD (Touati et al., 1983) and FeSOD (Sakamoto and Touati, 1984) of *E.coli* . The cloning of the MnSOD of BS and its expression in yeast has also been described (Bowler et al., 1990).

The present application further describes the cloning of the MnSOD of the Gram-positive thermophile *Bacillus caldotenax*, the determination of the entire nucleotide sequences of the MnSOD enzymes of both *Bacillus stearothermophilus* and *Bacillus caldotenax* and the overexpression of both enzymes in *E.coli*.

Thus the invention further provides a recombinant DNA molecule comprising a DNA sequence coding for a BC MnSOD enzyme as defined above.

Such recombinant DNA molecules may be selected from (a) the DNA coding sequence depicted in FIG. 12 (SEQ ID NO: 29) and (b) DNA sequences which are degenerate according to the genetic code to said sequence.

As indicated, we have now developed a procedure for overexpressing the MnSOD of BC and BS in *E.coli* which forms a further aspect of the present invention.

Thus according to a further aspect of the invention there is provided a process for producing an MnSOD enzyme which comprises culturing a transformed strain of *E.coli* containing a recombinant plasmid comprising at least one structural gene coding for an MnSOD enzyme operatively linked to a promoter, characterised in that said promoter is the native trp promoter of *E.coli*, or a related promoter having a base sequence related thereto, and differing therefrom only to such an extent that activity as a promoter is substantially retained.

Examples of specific promotor sequences are as follows:
(i) the sequence TTGACAATTAATCATCGAACTAGTTAACT (I)
(ii) a DNA sequence related to that of SEQ ID NO: 1, said related sequence differing from SEQ ID NO: 1 only to such an extent that activity as a promoter is essentially retained.
(iii) a DNA sequence having at least a 50% sequence homology, preferably at least 75% sequence homology, most preferably at least a 95% sequence homology with SEQ ID NO: 1.
(iv) sequences which differ from SEQ ID NO: 1 by not more than 10 deletions, preferably not more than 5 and most preferably not more than 2 insertions and/or substitutions.
(v) sequences as defined in (i)–(iv) composed of from between 12 to 50 bases, preferably between 20 to 35 bases, most preferably about 29 bases.
(vi) sequences as defined in (i)–(v) having a base sequence comprising the sequence TTGACA (SEQ ID NO: 2) at the 5' end and the sequence TTAACT (SEQ ID NO: 30) at the 3' end.
(vii) sequences as defined in (i)–(vi) having a base sequence comprising the sequence TCAATT (SEQ ID NO: 4) at the 5' end and the sequence ACAGTT (SEQ ID NO: 5) at the 3' end.
(viii) sequences as defined in (i)–(vii) having an intervening sequence located between said 3' and 5' sequences, said intervening sequence being selected from: ATTAATCATCGAACTAG (SEQ ID NO: 6) and related intervening sequences differing from the aforementioned sequence only to such an extent that activity as a promoter is essentially retained.
(ix) sequences as defined in (i)–(vii) having an intervening sequence which differs from the sequence ATTAATCATCGAACTAG (SEQ ID NO: 6) by not more than 10, preferably not more than 5 and most preferably not more than 2 deletions, insertions and/or substitutions.

The sequence TTGACAATTAATCATCGAACTAGTTAACT (SEQ ID NO: 1) may be preceded by the sequence GCTTACTCCCCATCCCCCCAGTGAATTCCCCTG (SEQ ID NO: 7) and followed by the sequence AGTACGCAGCTTGGC (SEQ ID NO: 8).

Appendix

Abbreviations: aa, amino acid(s); Ap, ampicillin; BCMnSOD, *Bacillus caldotenax* MnSOD; bp, base pair (s); BSMnSOD, *Bacillus stearothermophilus* MnSOD; CuSOD, copper-containing SOD; dal, daltons; FeSOD, iron-containing SOD; kb, kilobase(s) or 1000 bp; kcal, kilocalories; lacZ', gene encoding the b-galactosidase a-peptide; MnSOD, manganese-containing SOD; nt, nucleotide(s); oligo(s), oligodeoxynucleotide(s); ORF, open reading frame; ORI, origin of replication; 02-, superoxide radical; PAGE, polyacrylamide gel electrophoresis; par, plasmid pSC101 partition function;po, promoter operator region; PolIk, Klenow (large) fragment of *E.coli* DNA polymerase I; R, resistance; S, sensitive; SDS, sodium dodecyl sulfate; SOD, superoxide dismutase; sod, gene encoding for SOD; Tc, Tetracycline; vvm, volumetric volume per minute; wt, wild type; XGal, 5-bromo-4-chloro-3-indolyl-b-D-galactoside; ZnSOD, zinc-containing SOD.

BRIEF DESCRIPTION OF THE DRAWINGS

FIG. 1. Oligonucleotide probe used to detect the *B. stearothermophilus* sod gene.

The indicated amino acids (single letter code, upper line) (SEQ ID NO: 14) are residues 17 through 34 of t he sequence determined by Brock and Walker (1980). The 50 mer oligonucleotide synthesised (SEQ ID NO: 15) is labelled "probe", and was designed to complement the DNA strand encoding the targeted amino acid sequence. The actual sequence of the DNA encoding amino acids 17 through 34 is indicated above the oligonucleotide sequence (labelled "nt sequence") (SEQ ID NO: 13). Complementarity between the actual sequence and the probe is indicated by |, and neutral base pairing by a colon.

Figure 2:
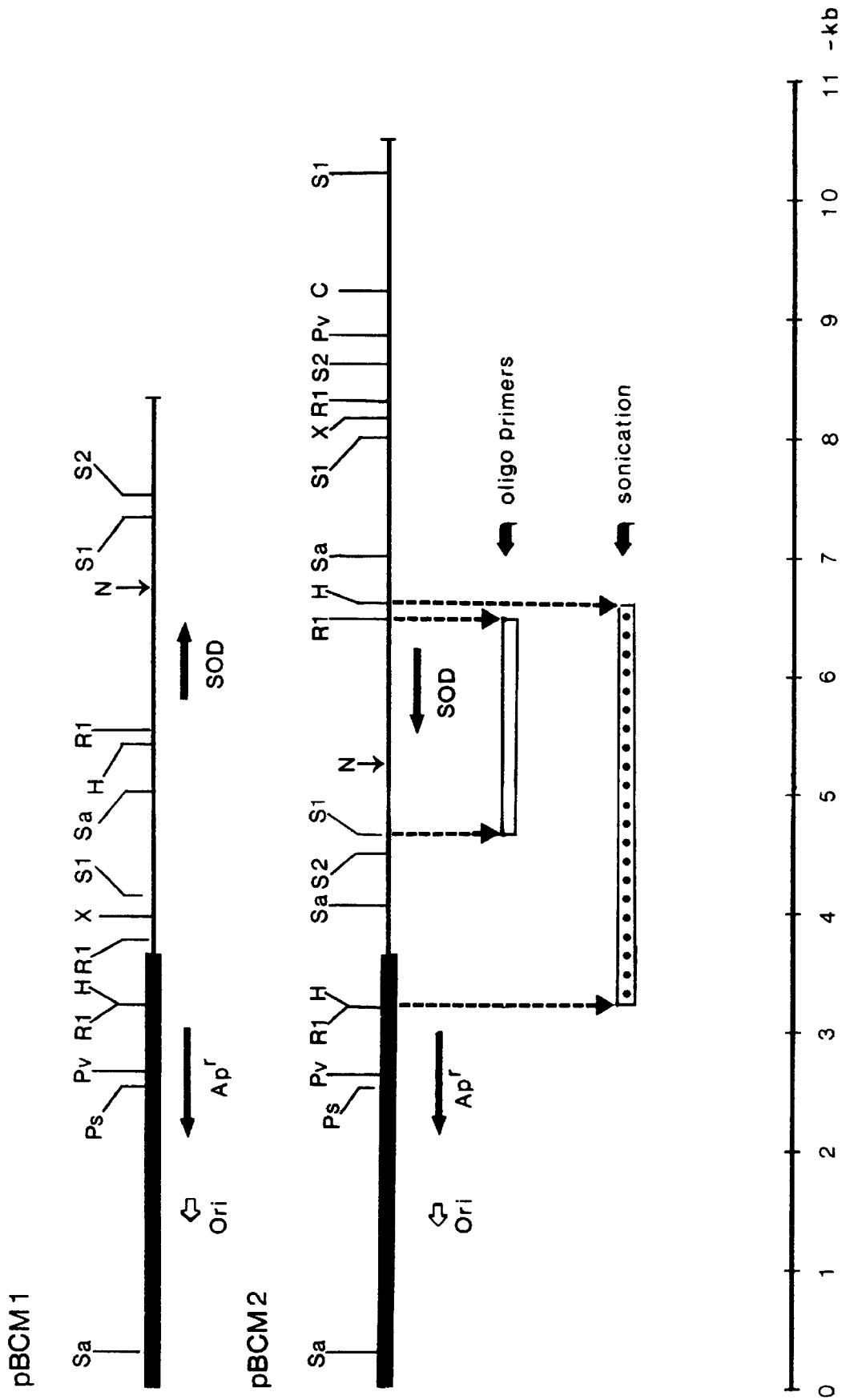

FIG. 2. Restriction enzyme map of pBCM1 and pBCM2.

Restriction enzyme sites are as indicated. DNA derived from pAT153 is represented by the thick line, the thin line representing the *B. stearothermophilus*-derived DNA insert. The positions and orientation of transcription of the sod (SOD) and bla (ApR) genes, and the ColE1 origin of replication (ORI) are marked by appropriate arrows. The indicated 3.0 kb HindIII fragment and the 1.6 kb EcoRI-SstI fragment were isolated for sequencing puposes as outlined in the text. Restriction enzyme sites are: C, ClaI; H, HindIII; N, NruI; P, PvuI; R1, EcoRI; Sa, SalI; S1, SstI; S2, SstII, and; X, XhoI.

FIG. 3. Nucleotide sequence of the *B. stearothermophilus* gene encoding MnSOD.

The illustrated region is a 1294 bp HindIII-NruI restriction fragment (SEQ ID NO: 16) derived from pBCM2 (see FIG. 2). Of the two ORFs, ORF A (SEQ ID NO: 17) corresponds to the sod gene and ORF B (SEQ ID NO: 18) to the unidentified putative gene. Possible ribosome binding sites preceding both ORFs are underlined and labelled S.D. The region of dyad symmetry, which may correspond to the transcriptional terminator of sod, is indicated by facing arrows above the sequence.

Figure 4:
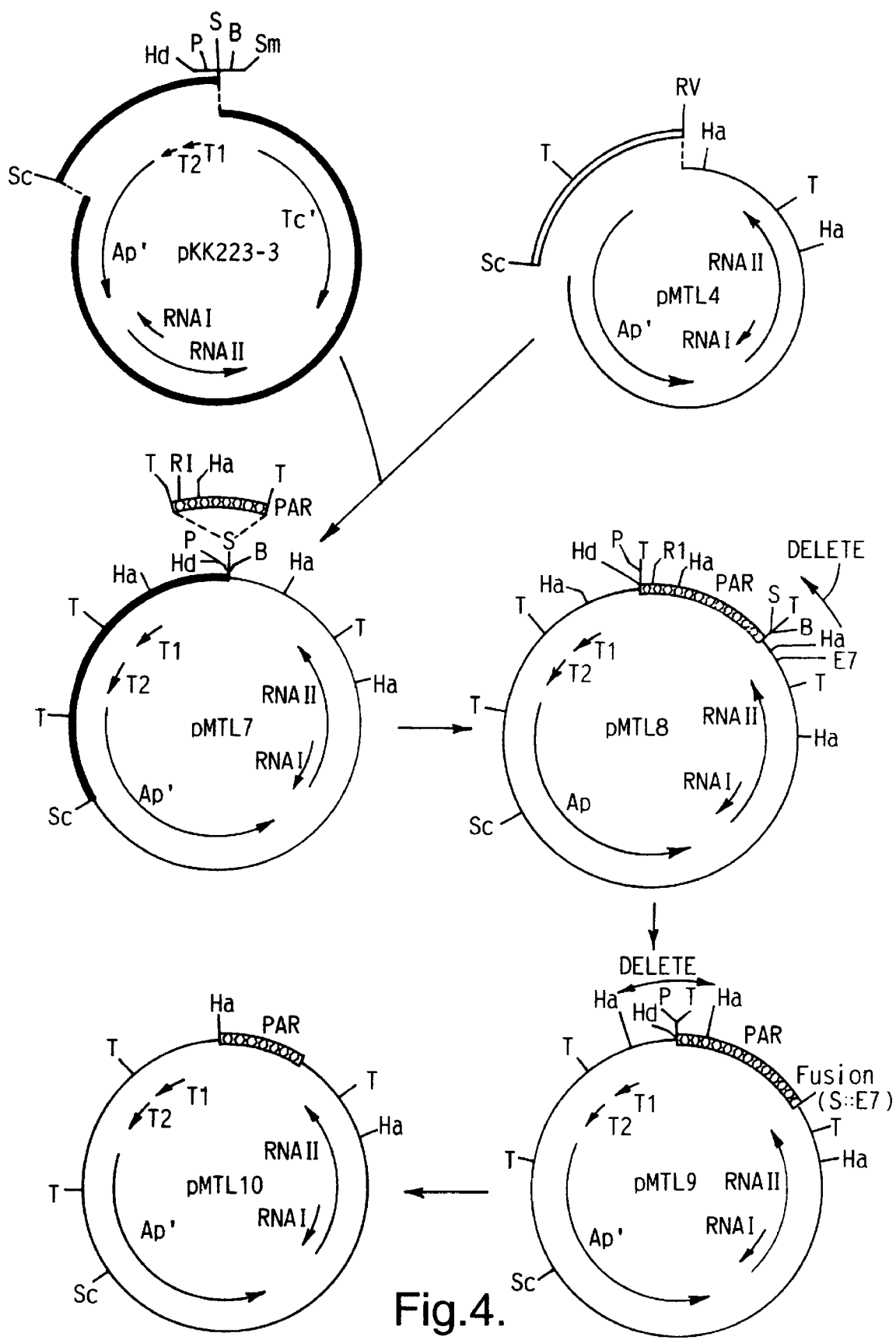

FIG. 4. Construction of pMTL10.

Details on the individual steps involved in the construction of pMTL4 are given in the text. Restriction enzyme sites are :-Sc, ScaI; Hd, HindIII; P, PstI; S, SalI; B, BamHI; Sm, SmaI; RV, EcoRV; E7, Eco47; R1, EcoRI; T, TaqI, and; Ha, HaeII. Other plasmid specified elements are: the ColE1 replication specific transcripts, RNA I and RNA II; the pSC101 partition function, PAR; the *E.coli* trp promoter, trp;

the b-galactosidase a-peptide, lacZ';, the *E.coli* rrnB operon transcriptional terminator signals, T1 and T2 and; the bla and tet genes, Ap and Tc.

Figure 5:
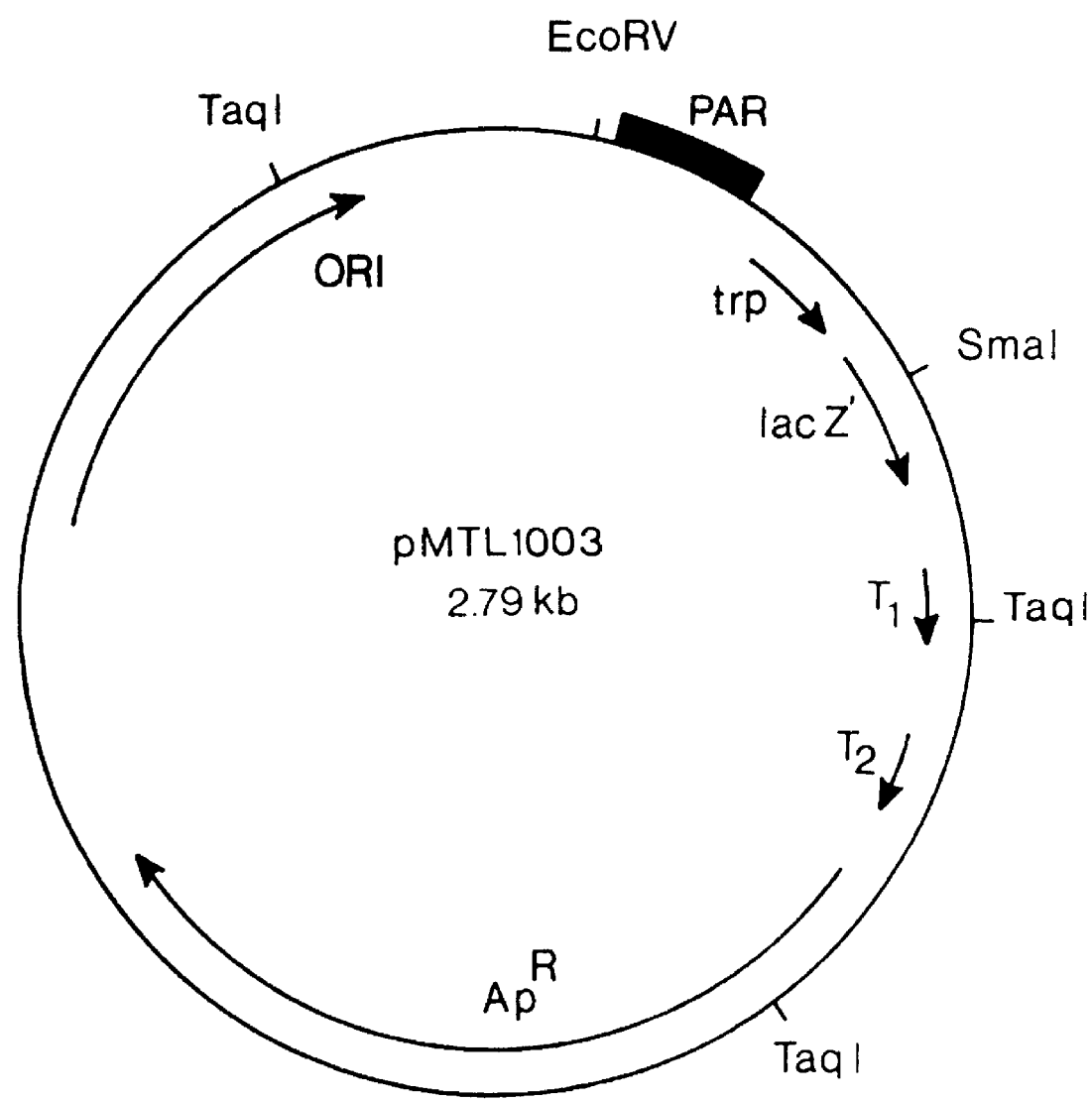

FIG. 5. Restriction enzyme map of pMTL1003.

Plasmid pMTL1003 was derived from pMTL10 (see FIG. 4) by the insertion of a 388 bp HaeII fragment carrying trp/lacZ'/polylinker into the HaeII site of pMTL10 immediately adjacent to the pSC101 par element (see text for details). Labelled elements are: the ColE1 replication origin, ORI; the pSC101 partition function, PAR; the *E. coli* trp promoter, trp; the b-galactosidase a-peptide, lacZ'; the ampicillin resistance gene (bla), ApR, and; the *E.coli* rrnB operon transcriptional terminator signals, T1 and T2.

FIG. 6. Nucleotide sequence of the polylinker cloning region of pMTL28

The indicated polylinker regions (SEQ ID NO.s: 19, 20 and 22–27) correspond to those available in the pMTL20 cloning vector series (Chambers et al., 1988). The five amino acid sequence MTMIT is SEQ ID NO: 21. pMTL28 was derived by chemically synthesising the appropriate oligos (5'-TCGAGATCTCCCGGGATCCGATATCTGATC-AGTTAACAGATCTG-3' (SEQ ID NO: 11) and 5'-AATT-CAGATCTGTTAACTCATCAGATATCGGATCCCGG-GAGATC-3' (SEQ ID NO: 12)), annealing them and inserting them between the XhoI and EcoRI sites of pMTL23.

Figure 7:
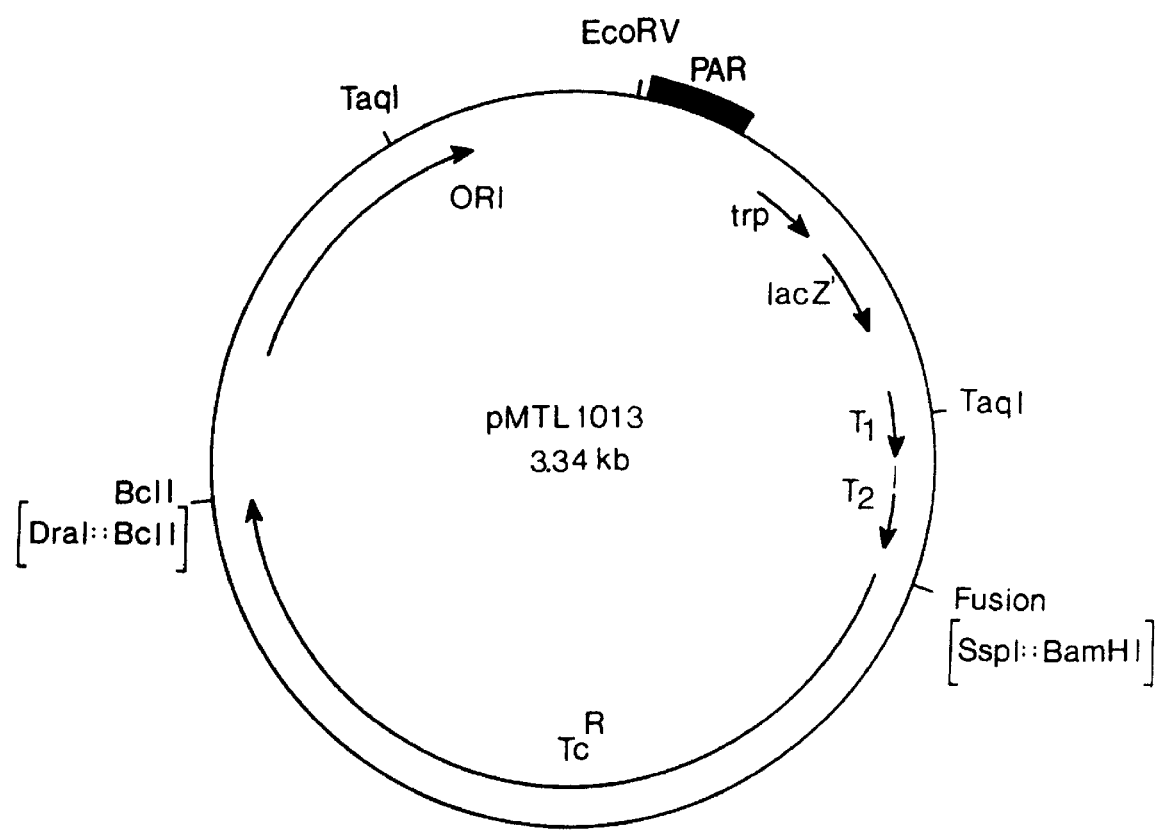

FIG. 7. Restriction enzyme map of pMTL1013

Plasmid pMTL1013 was constructed from pMTL1003 by substituting the bla gene with the tet gene (see text for details). Labelled elements are: the ColE1 replication origin, ORI; the pSC101 partition function, PAR; the *E.coli* trp promoter, trp; the b-galactosidase a-peptide, lacZ'; the tetracycline resistance gene (tet), TcR, and; the *E.coli* rrnB operon transcriptional terminator signals, T1 and T2.

Figure 8:
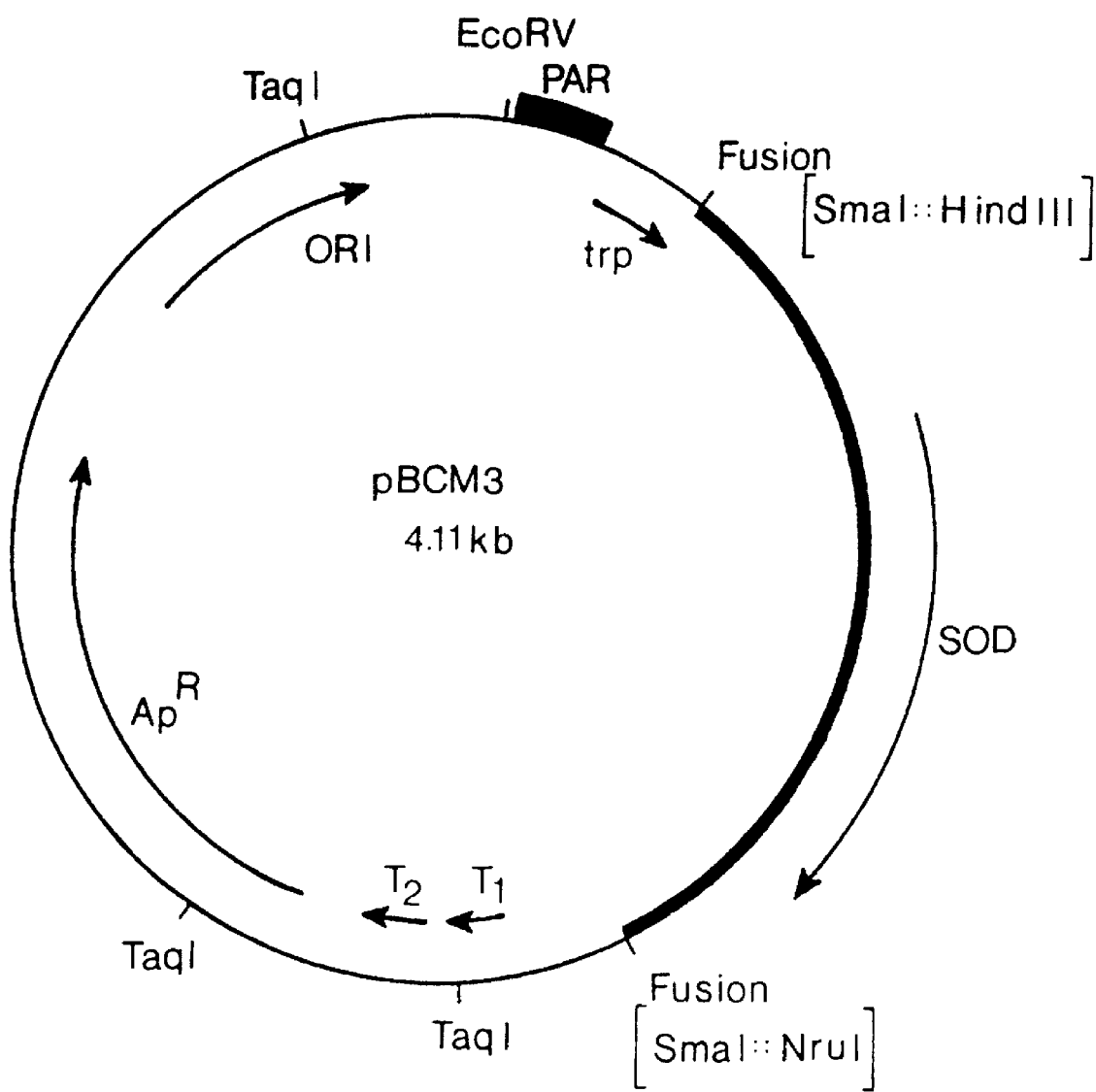

FIG. 8. Restriction enzyme map of pBCM3

Plasmid pBCM3 was constructed by isolating the sod gene pBCM2 as a 1.3 kb NruI-HindIII fragment (FIG. 3), cloning it between the SmaI and HindIII restriction sites of pUC9 and then re-excised as a similarly sized EcoRI-HindIII fragment. This fragment was then inserted, following blunt-ending by treatment with PolIk, into SmaI site of the pMTL1003, such that transcriptional readthrough of sod could occur from the vector trp promoter. The *B.stearothermopilus*-derived DNA insert is represented by the thick line. Other features are: ColE1 origin of replication, ORI; pSC101 partition function, PAR; trp promoter, trp; rrnB transcriptional terminators, T1 and T2; ampicillin resistance marker and; the *B. stearothermophilus* MnSOD gene, SOD.

Figure 9:
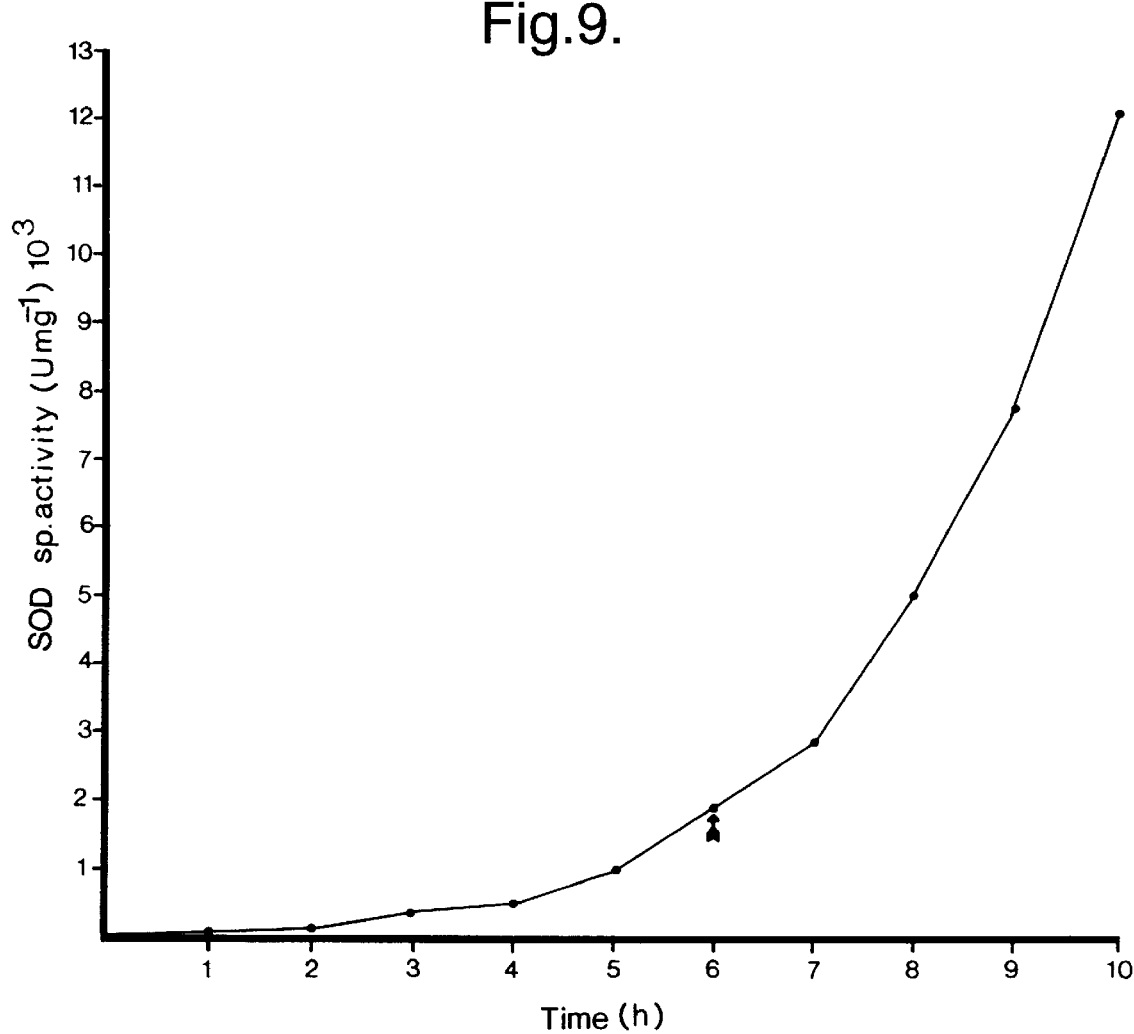

FIG. 9. Production of recombinant MnSOD in *Escherichia coli* carrying pBCM3

Cells harbouring pBCM3 were grown in complex media (2XYT), supplemented with 100 1M MnSO$_4$, and transcription from the vector trp promoter induced in late exponential phase (indicated by an arrow) by the addition of indole acrylic acid (20 lg/ml). Cells were removed from the cultures at hourly intervals, disrupted by sonication and the SOD activity of the extract determined following removal of cell debris by centrifugation.

Figure 10:
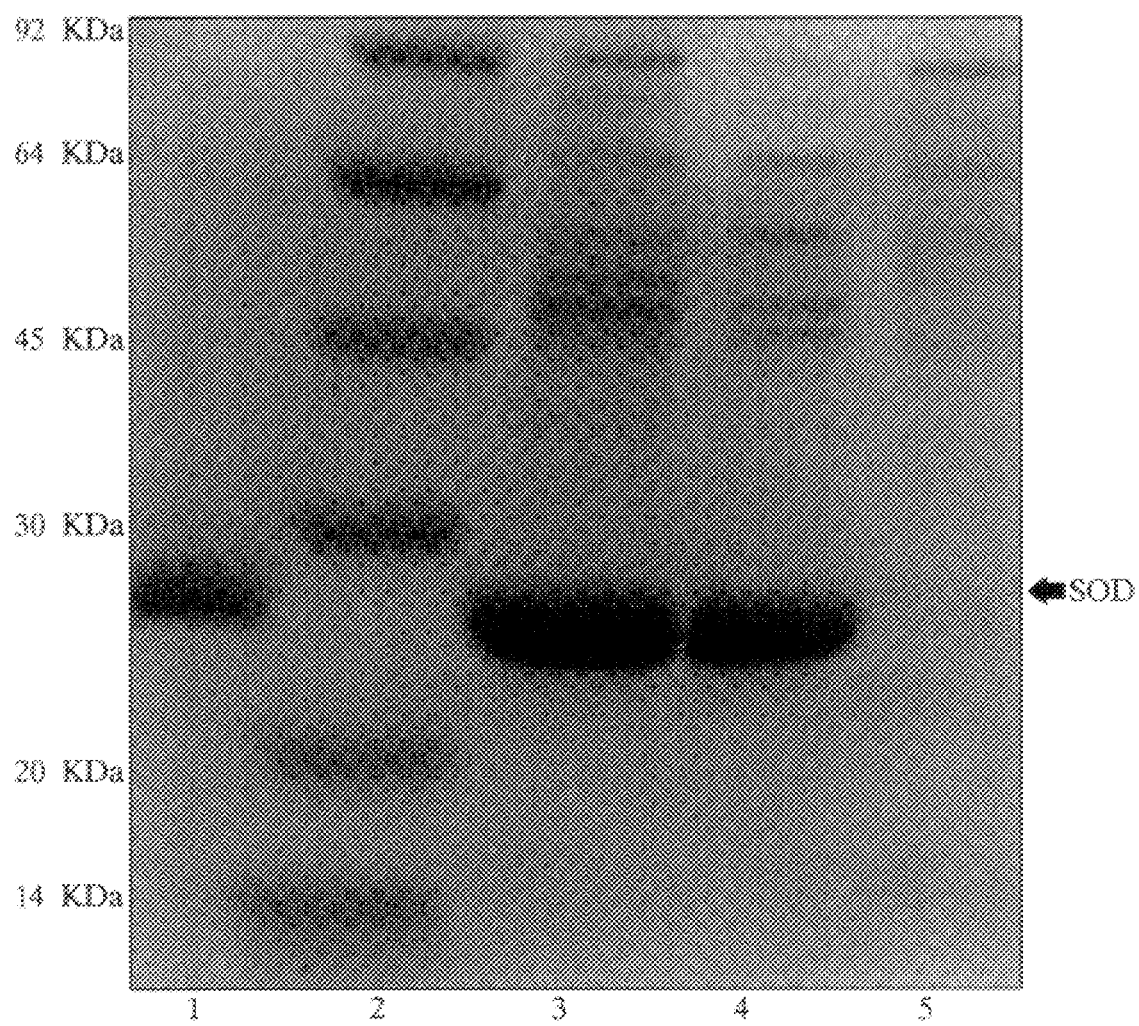

FIG. 10. SDS-PAGE of total cell extracts of TG1 cells carrying pBCM3

Total cell extracts were derived from the 10 h sample of the experiment oultined in FIG. 9, and subjected to SDS-PAGE. Lane 1, purified *B. stearothermophilus* MnSOD; lane 2, molecular weight markers, and; lane 3, soluble cell lysate of TG1 carrying pBCM3.

Figure 11:
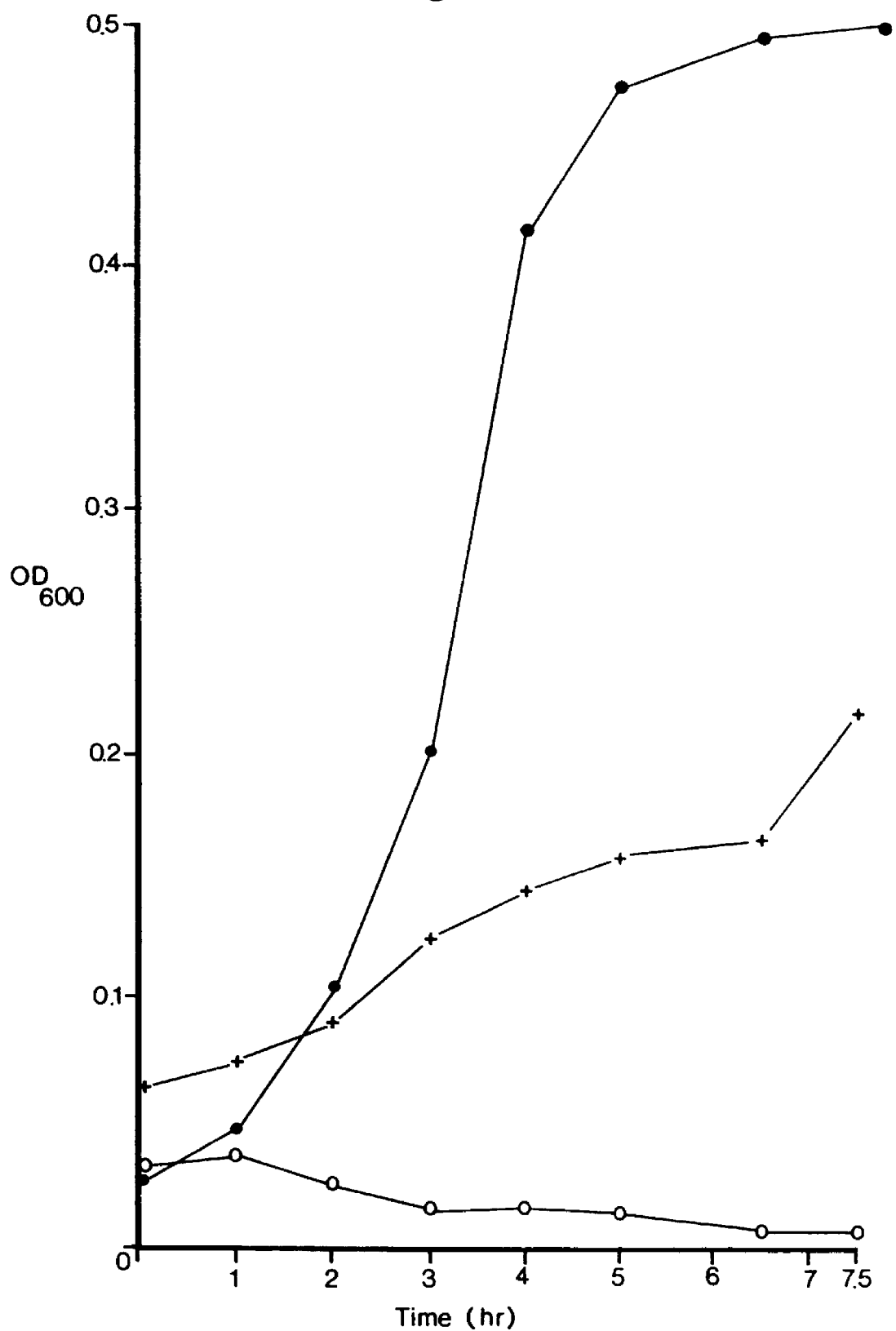

FIG. 11. The ability of pBCM3 to complement an *E.coli* sodA mutant.

Strain QC781 was grown in the presence of 10-5 methyl viologen, either containing (+) or not containing (o) plasmid pBCM3. A growth curve of plasmid-free QC781 ( ) is also included for comparative purposes.

FIG. 12. Nucleotide sequence of the *B. caldotenax* gene encoding BCMnSOD (SEQ ID NO: 29)

The illustrated region (SEQ ID NO: 28) is a 780 bp portion of the 1.9 kb AccI fragment carried by pBCM8. Nucleotide sequence differences which occur in the *B. stearothermophilus* sequence are shown above the sequence in lower case (the '–' indicates the absence of a nucleotide in the *B. stearothermophilus* DNA). The two amino acid differences between BSMnSOD (SEQ ID NO: 17) and BCMnSOD (SEQ ID NO: 29) are illustrated by including the BSMnSOD (SEQ ID NO: 17) amino acids below the BCMnSOD (SEQ ID NO: 29) sequence at the appropriate positions (103, Asp instead of Glu; 188 Val in place of Ile). The ribosome binding site preceding the sod gene is underlined and labelled S.D. The region of dyad symmetry, which may correspond to the transcriptional terminator of sod, is indicated by facing arrows above the sequence.

Figure 13:
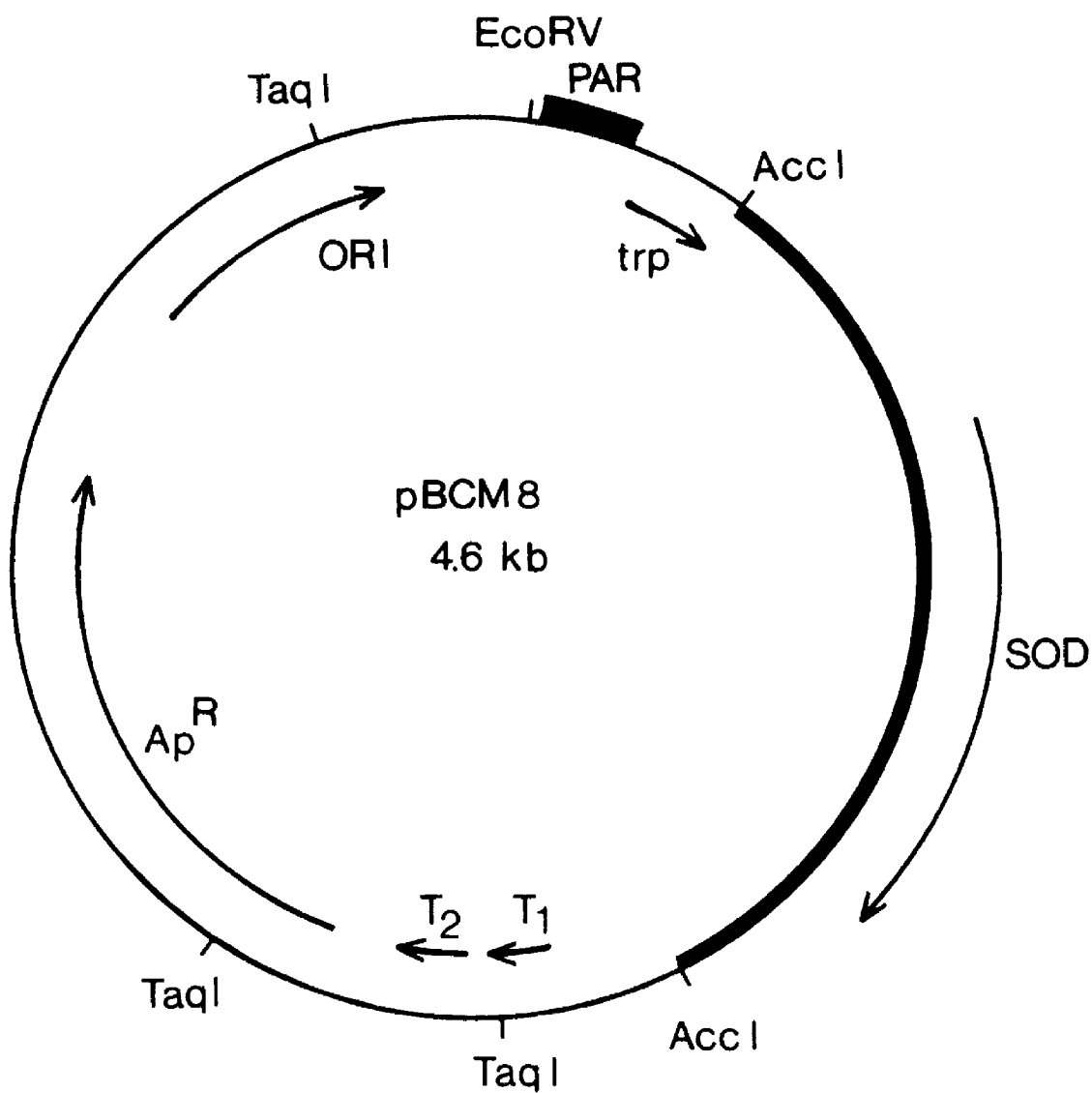

FIG. 13. Restriction enzyme map of pBCM8

Plasmid pBCM8 was constructed by isolating the *B. caldotenax* sod gene from pBCM7 as a 1.9 kb AccI-fragment and cloning it into the AccI restriction site of the pMTL1003, such that transcriptional readthrough of sod could occur from the vector trp promoter. The *B. caldotenax*-derived DNA insert is represented by the thick line. Other features are: ColE1 origin of replication, ORI; pSC101 partition function, PAR; trp promoter, trp; rrnB transcriptional terminators, T1 and T2; ampicillin resistance marker and; the *B. caldotenax* MnSOD gene, SOD.

DETAILED DESCRIPTION OF THE INVENTION

The following protocol was adopted for the molecular cloning of the *B. stearothermophilus* sod gene.

The first step in the cloning of the encoding gene was to design an oligonucleotide which demonstrated sufficient homology to the structural gene to allow its detection by DNA/DNA hybridisation experiments. Analysis of the amino acid sequence indicated that amino acids 17 through 34 represented a peptide exhibiting minimal translational degeneracy. Accordingly, a 50 mer antisense oligonucleotide was synthesised (FIG. 1) in which nucleotide bases used in positions of codon degeneracy corresponded to those most frequently used in *B. stearothermophilus* genes. To test that the synthesised oligonucleotide hybridised to a specific sequence in the *B.stearothermophilus* genome, Southern blot experiments were undertaken. The oligonucleotide was radiolabelled and used in DNA/DNA hybridisation reactions against *B. stearothermophilus* NCA1503 genomic DNA cleaved with various restriction enzymes.

Under the conditions employed (see the Examples below) the probe was shown to hybridise strongly to the following discrete restriction fragments; a 2.45 kb BclI, 5.1 kb ClaI, 6.8 kb EcoRI, 3.4 kb HindIII, 20 kb PstI, 3.2 kb SalI, 3.5 kb SstI and a 17 kb XhoI fragment.

Having demonstrated the specificity of the oligonucleotide probe, a plasmid library of the *B. stearothermophilus* genome was constructed by ligating sized (approx. 8 kb), partially digested (Sau3a) chromosomal DNA with BamHI-cleaved pAT153 DNA. The resultant ligation mixtures were transformed into E.coli W5445 and transformants selected on L-agar containing ampicillin. Of the 6,000 ApR transformants obtained, 4,125 proved to be TcS. Upon analysis of the plasmids of 50 random representatives of the 4,125 presumptive recombinant clones, 46 were shown to contain inserts. Each ApR TcS recombinant clone was individually screened by in situ colony hybridisation, using the radiolabelled oligonucleotide as a probe. The probe was shown to hybridise strongly to two different recombinant clones. Plasmid DNA was isolated from each clone and designated pBCM1 and pBCM2. A restriction map of these two plasmids is illustrated in FIG. 2. These maps demonstrate that the insert of pBCM1 was 4.7 kb, while that of pBCM2 was 6.85 kb in size. Comparative analysis of DNA fragments generated by digestion (singularly or in double combinations) with various restriction enzymes indicated that the insert of pBCM2 entirely encompassed that of pBCM1, and furthermore, that the insert of pBCM1 was in the opposite orientation, relative to the vector, to that of pBCM2.

In order to localise the position of the sod structural gene within cloned DNA present in pBCM1 and pBCM2, each plasmid was restricted with various endonucleases and the resultant fragments subjected to Southern blot analysis. One of the smallest restriction fragment which hybridised to the oligo probe was shown to be a 1.6 kb EcoRISs tI fragment common to both plasmids.

Accordingly this fragment was gel purified from pBCM2 DNA and ligated to M13mp18 and M13mp19 similarly cleaved with EcoRI and SstI. The ligation mixes were transformed into E.coli TG1 and plated on 2XYT agar in H-top agar overlays containing XGal and IPTG. Recombinant plaques, identified by their colourless appearance, were utilised to prepare template DNA. Representative templates derived from each M13 vector were than subjected to nucleotide sequence analysis using universal primer. Translation of the DNA sequence obtained from both templates into amino acid sequence failed to yield an ORF encoding a polypeptide homologous to the published MnSOD sequence. This suggested that sod resided within the central portion of this fragment. Thereafter, the complete sequence of the insert was determined using two different strategies: (i) oligonucleotides specific to the sequence derived from the above two templates were synthesised and used to extend the previously determined sequence; (ii) the 3.0 kb HindIII fragment of pBCM2 which encompasses the cloned 1.6 kb EcoRI-SstI fragment was isolated by electroelution, circularised by self-ligation, fragmented by sonication, the staggered ends generated blunt-ended by treatment with T4 polymerase, and gel purified fragments of 500 to 1000 bp inserted into the SmaI site of M13mp8.

Template DNA was prepared from 100 of the recombinant clones obtained. The nucleotide sequence data obtained was assembled into one contiguous sequence using the computer software of DNASTAR Inc. The sequence illustrated in FIG. 3 represents a 1294 bp portion of the sequence obtained which encompasses the sod structural gene, and was determined on both DNA strands.

Translation of the nucleotide sequence illustrated in FIG. 3 revealed the presence of an ORF of 615 bp beginning with an AUG codon (nt 387) and terminating with a UAA codon (nt 1001). The deduced polypeptide was 204 aa in length and, with the exception of the N-terminal Met, exhibited perfect conformity to the experimentally determined aa sequence of MnSOD (Brock and Walker, 1980).

A sequence beginning at 438 and ending at 488 exhibited near perfect complimentarity to the oligo probe utilised to identify the gene. The three positions at which mismatch occurred (nt.465, 477 and 483) all resulted in neutral G.T pairing, accounting for efficient binding of the oligo to B.stearothermophilus-derived DNA encoding sod. The translational initiation codon was preceded by a sequence (5'-CAAAAGGAGGAGA-3') (SEQ ID NO: 9) exhibiting strong complimentarity to the 3'-termini of the Bacillus subtilis 16S rRNA (3'-UCUUUCCUCCACU-5') (SEQ ID NO: 10). A sequence exhibiting dyad symmetry occurs immediately 3' to the translational stop codon (nt 1007 to 1036), and probably represents a Rho-independent transcriptional terminator. The putative RNA stem-loop structure formed would have a DG of −22.2 kcal. A second putative ORF was identified 3' to sod, initiating with an AUG codon at nt 1133 and preceded by a sequence exhibiting reasonable complimentarity to the B.subtilis 16S rRNA. The encoded putative polypeptide exhibits no homology to any protein currently found in the PIR database. The sod structural gene exhibits a G+C content of 53.1%, and its codon usage is illustrated in Table 2.

To elicit the overexpression of sod in E.coli use was made of the plasmids pMTL1003 and pMTL1013, part of a series of expression vectors recently constructed in this laboratory. Derived from pMTL4 (Chambers et al., 1988), pMTL1003 replicates from a mutant ColE1 replicon (600 copies per cell; Minton et al., 1988), encodes pUC8-derived bla and lacZ' (Messing and Vieria, 1982), and incorporates the pSC101 partition function (par; Miller et al., 1983), the E.coli rrnB double terminator (Brosius et al., 1981) and the pMTL20 polylinker cloning region (Chambers et al., 1988). Transcription of lacZ' is under the control of a synthetic trp promoter. pMTL1013 differs from pMTL1003 only in that the bla gene (ApR) has been replaced with the tet (TcR) gene. These expression vectors were derived in the following manner (see FIG. 4 for details).

The 5' end of the bla gene (ApR) was isolated, together with the double transcriptional termination signals (T1 and T2) of the rrnB operon, from the plasmid pKK223-3 as a 831 bp ScaI/SmaI fragment, and inserted between the EcoRV and ScaI sites of pMTL4, to give pMTL7. A 385 bp TaqI fragment carrying the pSC101 par stability determinant (Miller et al., 1983) was then inserted between the EcoRV and ScaI sites to yield pMTL8. The remaining manipulations were designed to both reduce the size and remove unwanted restriction sites from the final vector. pMTL8 was cleaved with SalI and Eco47, blunt-ended with S1 nuclease and self-ligated to give pMTL9. This 58 bp deletion removed the unique SalI, Eco47, and BamHI sites and a number of TaqI and HaeII sites. A 322 bp HaeII fragment was then deleted from pMTL9, reducing the number of HaeII and TaqI sites in the final vector, pMTL10, by one, and removing the unique PstI and HindIII sites. Although this deletion removed part of the pSC101 par fragment, pMTL10 was shown experimentally to exhibit 100% segregationally stability in cells grown in the absence of antibiotic selection. The final modification made to the basic vector backbone was to employ site-directed mutagenesis to introduce a unique EcoRV site between par and the ColE1 origin of replication.

This was achieved by first cloning the 530 kb TaqI fragment of pMTL10 encompassing this region into the AccI site of M13mp8. A mutagenic oligonucleotide was then employed to introduce the desired EcoRV restriction site using site-directed mutagenesis. The mutated TaqI fragment was then reisolated and ligated to the 1.44 kb and 430 kb TaqI fragments of pMTL10. The modified vector obtained was designated pMTL100.

In order to place the expression of a heterologous gene under the transcriptional control of an extraneous promoter it is necessary to insert the structural gene in the correct orientation adjacent to the appropriate transcriptional signals. Such manipulative procedures are enhanced by the facility for directional cloning and by the existence of a means of detecting the insertion of the foreign DNA.

One of the simplest systems, exemplified by the pUC and M13 series of vectors (Vieira and Messing, 1982) is that involving inactivation of the b-galactosidase a-peptide encoded by lacZ'. Vectors carrying a functional lacZ' confer a blue colouration to the colonies or plaques of appropriate E.coli hosts in the presence of the chromogenic substrate XGal. Inactivation of the gene (ie., by the insertion of heterologous DNA) results in the colourless (white) colonies/plaques. In the pUC and M13 vectors, the lacZ' gene is proceeded by its natural lac po promoter region.

In the vectors pMTL1003 and pMTL1013, we wished to retain the utility of the lacZ' selection system but replace the lac promoter with that of the trp promoter. To achieve this site-directed mutagenesis of M13mt120 DNA was used to remove a PvuII site within the 3' end of lacZ' (leaving the PvuII site 5' to the lac po unique) and to create a unique HpaI site 3' to the +1 of the lac po at the same time an NdeI site was created at the start of the lacZ' gene, such that the ATG of the NdeI recognition sequence (CATATG) corresponded to the AUG translational initiation codon of lacZ'.

Although not relevant to the expression of SOD, its presence will aid in the future expression of other genes. eg., an NdeI site may be created at the equivalent position in any heterologous gene to be expressed, and then used to insert the gene at the NdeI site of the modified lacZ'. This places the AUG start codon of the gene to be expressed at the optimum distance from the Shine-Dalgarno of the lacZ' gene, maximising subsequent translational of RNA transcripts. A 830 bp HindIII-PstI restriction fragment carrying a synthetic E. coli trp promoter was isolated from plasmid pDR720 (Russell and Bennett 1982), blunt-ended by treatment with PolIk and inserted between the PvuII and HpaI sites of the modified M13mtl120 vector. This manipulation effectively substituted the natural lac promoter with that of trp [NB. the same strategy may be employed to replace lac po with any other promoter element]. The trp promoter/lacZ'/polylinker region was then removed from the M13 vector as a 388 bp HaeII fragment and cloned into one of the two HaeII sites of pMTL100, in the indicated orientation (FIG. 5) to give pMTL1003.

The vector pMTL1013 is analogous to pMTL1003, except that the bla gene has been replaced with the pBR322 tet gene. The tet gene was isolated from pBR322 as a 1.43 kb EcoRI-AvaI fragment (Balbas et al., 1986), blunt-ended with PolIk and inserted into the SmaI site of M13mp10. Site-directed mutagenesis was then employed. to remove restriction enzyme sites for ClaI, HindIII, EcoRV, BamHI, SphI, and SalI. The respective nucleotide substitutions were: A to T, nt 27; T to A, nt 28; T to C, nt 187; C to T, nt 379; T to C, nt 565, and; C to T, nt 656 (nucleotide positions correspond to the pBR322 sequence, Balbas et al., 1986). The modified tet gene was then excised as a approx. 1.43 kb EcoRI-BamHI fragment inserted into the HpaI site of pMTL28 (see FIG. 6), re-isolated as a BamHI-BclI fragment and ligated to a 1.85 kb fragment of pMTL1003 generated by cleavage of pMTL1003 with SspI and DraI. The final plasmid obtained was designated pMTL1013 (FIG. 7).

The sod gene was isolated from pBCM2 as a 1.3 kb NruI-HindIII fragment (FIG. 3), cloned between the SmaI and HindIII restriction sites of pUC9 and then re-excised as a similarly sized EcoRI-HindIII fragment. This fragment was then inserted, following blunt-ending by treatment with PolIk, into SmaI site of the pMTL1003. Two recombinant plasmids (pBCM3 and pBCM4), representing the two possible orientations of insertion of the cloned fragment, were chosen for further study. In the case of pBCM3 (FIG. 8), sod was orientated such that its expression could be enhanced by transcriptional read-through from the vector trp promoter. Two analogous plasmids pBCM5 (equivalent to pBCM3) and pBCM6 (equivalent to pBCM4) were generated by using pMTL1013 in place of pMTL1003.

Cells harbouring pBCM3 and pBCM4 were grown in complex media (2XYT), supplemented with 100 1M MnSO$_4$, and transcription from the vector trp promoter induced in late exponential phase by the addition of indole acrylic acid (20 lg/ml). Cells were removed from the cultures at hourly intervals, disrupted by sonication and the SOD activity of the extract determined following removal of cell debris by centrifugation.

The maximum level of MnSOD produced by cells carrying pBCM3, 62,275 units per ml of culture (equivalent to 12,210 u/mg soluble protein), was attained after 10 h (FIG. 9). By reference to the specific activity of pure MnSOD (25,000 u/mg), this equated to 47% of the cells soluble protein. Confirmation of these levels was obtained by densiometric scanning of Coomassie blue stained gels following SDS-PAGE of total cell extracts (see FIG. 10).

That high expression was due to the vector trp promoter was indicated by the low level of SOD produced (10.9 units per ml of culture) by cells harbouring pBCM4. The surprising ability of E.coli to support high level of expression of the B.stearothermophilus sod gene is consistent with the observation that its encoding region makes little use of modulator codons (a single CGG and a GGA codon are used), exhibits a codon bias characteristic of highly expressed E.coli genes and is preceded by a near to consensus ribosome binding site.

The levels of sod expression directed by pBCM3 were examined in a range of E.coli hosts with varying degrees of native SOD activity (Table 3). In this case transcription from the trp promoter was induced late in their exponential phase following tryptophan depletion from the minmal salts medium described in the Examples. Inexplicably, hosts carrying a mutant sodB locus produced significantly lower levels of recombinant SOD than either a soda or wt host.

Previous studies have shown that sod mutants exhibit enhanced sensitivity to methyl viologen (Carlioz and Touati, 1986), a commercial weed killer known to generate superoxide free radicals in E.coli . It was therefore of interest to see whether the B. stearothermophilus enzyme was capable of complementing the enhanced sensitivity of the E.coli strain QC781 to methyl viologen. Strain QC781 with and without pBCM3 was therefore grown in the presence of 10-5M methyl viologen and the effect on growth rate quantified. The results are illustrated in FIG. 11. Expression of recombinant SOD was seen to alleviate the growth inhibitory effect of the drug, but did not completely restore growth rates to those attained by QC781 in the absence of methyl viologen. This is in contrast to similar experiments undertaken with a cloned yeast MnSOD (Schrank et al., 1988).

The production of the MnSOD gene of B stearothermophilus and B. caldotenax will be described in more detail in the following examples. The bacterial strains and recombinant vectors utilised are listed in Table I.

EXAMPLE 1

(a) Media and Culture Conditions

B. stearothermophilus was grown at 58° C. and pH of 7.0 with an air flow rate of 1 vvm in the following medium;

sucrose (4%), yeast extract (5%), KH$_2$PO$_4$ (1%), MgSO$_4$.7H$_2$O (0.054%), MnCl$_2$.4H$_2$O (0.003%), FeCl$_3$.H$_2$O (0.0014%), citric acid monohydrate (0.064%), polypropylene glycol P-2000 (0.01%). *E.coli* was routinely cultured in L-broth (1% tryptone, 0.5% yeast extract, 0.5% NaCl). Solidified medium (L-agar) consisted of L-broth with the addition of 2% (w/v) agar (Bacto-Difco). Antibiotic concentrations used for the maintenance and the selection of transformants were 50 lg/ml ampicillin, 15 lg/ml tetracycline, 30 lg/ml kanamycin and 5 lg/ml chloramphenicol. Repression of the trp promoter, when necessary, was obtained by the presence of an excess of tryptophan in the media (100 lg/ml). The medium used in the pilot scale production of recombinant SOD in *E.coli* contained glucose (1.4%), NH$_4$SO$_4$ (0.25%), KH$_2$P$_4$ (0.3%), K$_2$HPO$_4$ (0.2%), Na.citrate (0.005%), yeast extract-Difco (0.5%), MgSO$_4$ (1%) and trace elements (1.0%). Stock solution of trace elements EDTA.Na$_2$ (0.5%), FeCl$_3$.6H$_2$O (0.05%), ZnO (0.005%), CuCl$_2$.H$_2$O (0.001%), CoNO3.6H$_2$O (0.001%) and NH$_4$Mo$_7$O$_{24}$ (0.001%). The culture was grown at 37° C. at a pH 7.0 +0.1 with an air flow rate of 1 vvm. Under these conditions exponential growth ceased after about 8 hours at which time the culture was harvested.

(b) Purification of DNA

Plasmids were purified from cleared lysates prepared using a Brij-lysis procedure (Clewell et al., 1969) and subsequent caesium chloride-ethidium bromide density gradient centrifugation (Colman et al., 1978). A rapid, small scale plasmid purification technique (Holmes and Quigley, 1981) was also employed for screening purposes. Chromosomal DNA from the donor *B.stearothermophilus* was prepared essentially as described by Marmur (1961).

(c) Restriction, Ligation and Transformation Methods

Restriction endonucleases and DNA ligase were purchased from Bethesda Research Laboratories (BRL) and used in the buffers and under the conditions recommended by the supplier. Transformation of *E.coli* was essentially as described by Cohen et al. (1972).

(d) Agarose Gel Electrophoresis

Digests were electrophoresed in 1% agarose slab gels on a standard horizontal system (BRL Model H4), employing Tris-borate-EDTA buffer. Electrophoresis of undigested DNA was at 125 V, 50 mA for 3 h, while digested DNA was-electrophoresed at 15 V, 10 mA for 16 h. Fragment sizes were estimated by comparison with fragments of phage k DNA cut with both HindIII and EcoRI. Fragments were isolated from gels using electroelution (McDonnell et al., 1977).

(e) Nucleotide Sequencing

M13 bacteriophage clones were sequenced by the dideoxynucleotide method of Sanger et al (1977) using a modified version of bacteriophage T7 DNA polymerase, "sequenaseR" (Tabor and Richardson, 1987). Experimental conditions used were as stated by the supplier (USB Corp.). Sequencing of double-stranded plasmid DNA was by a modification of the Klenow polymerase-dideoxynucleotide method developed by Chen and Seeburg (1985). Experimental conditions used were as stated by the supplier (BCL).

(f) Southern Transfer of DNA

DNA restriction fragments were transferred from agarose gels to "zeta probe" nylon membrane by the method of Reed and Mann (1985). Gels were partially depurinated with 0.25M HCL (15 min) prior to transfer in 0.4M NaOH transfer solution. Transfer was carried out for 4–16 h by capillary elution prior to hybridisation.

(g) In Situ Colony Hybridisations

Bacterial colonies were screened for desired recombinant plasmids by in situ colony hybridisation as described by Grunstein and Hogness (1977), using nitrocellulose filter disks (Schleicher and Schull, 0.22 lm).

(h) Radiolabelling of Oligonucleotides

Oligonucleotide probes were end-labelled by the addition of [c-32P] dATP to the 5'-hydroxyl terminal with T4 polynucleotide kinase (Maxam and Gilbert, 1977). Unincorporated nucleotides were removed by chromatography through sephadex G-25 disposable columns as specified by the manufacturer (Pharmacia).

(i) Hybridisation Conditions

Hybridisations using the 5'-end-labelled 50 mer oligonucleotide probe were carried as described by Sambrook et al (1989) at a temperature of 55° C. for 2 or more h. Filter washes were carried out at 45° C., several times of 5 min duration.

(j) Site-directed Mutagenesis

Coupled priming oligonucleotide-directed mutagenesis was carried out using the suppressor selection protocol of Carter et al (1985). Mutants were identified by the differential temperature hybridisation method described by Carter et al (1984) using radiolabelled oligonucleotide as probe.

(k) Segregational Stability

The segregational stability of plasmid vectors was analysed using continuous culture. Cells were grown in a LH500 series fermenter and control package in a 1 litre continuous culture vessel in a working volume of 600 ml. The growth medium employed was the simple salts medium of Tempest (1969). Cultures were maintained at 37° C., pH 7.0 and with an aeration rate of 1 vvm. Following inoculation, cultures were allowed to grow batchwise for 4 to 5 h before the flow of fresh medium was initiated. Samples were removed periodically and serially diluted onto isosensitest agar and colonies, screened for plasmid encoded b-lactamase production.

(1) Determination of Superoxide Dismutase Activity

Bacteria were grown in 1 liter batch culture and 100 ml samples taken at various stages in the growth phase. Samples were cooled on ice, centrifuged 13,000 g for 120 minutes and resuspended and frozen in 5 ml 50mM Phosphate buffer (pH 7.8). The cells were disrupted using a MSE Ultrasonic Disintegrator (150 W) at medium frequency, amplitude 2, for three .30 second intervals on ice. Cell debris was removed by centrifugation at 10,000 g for 5 minutes. SOD activity was measured by monitoring the inhibition of reduction of ferric cytochrome C, as described by McCord and Fridovich (1979). Protein concentration was determined by the method of Bradford (1976). SOD activity was also visualised following PAGE, the gel was soaked in a solution of nitro-blue tetrazolium reagent before adding riboflavin. This procedure was fully described by Beauchamp and Fridovich (1971).

(m) Small-scale Fermentation of E.coli TG1 Containing pBCM3

Although the level of expression of recombinant SOD obtained in batch culture was of a high order of magnitude, it was of interest to see whether high production rates could be translated to conditions more closely resembling those employed for commercial production of recombinant proteins. Accordingly, an 8 l pilot-scale culture was carried out using the minimal salts medium described herein. The inoculum for the seed was provided by freshly transformed cells plated out onto L-agar supplemented with tryptophan (100 lg/ml) and ampicillin (100 lg/ml) for promoter repression and selection, respectively. The seed was provided by a 500 ml 2×LB culture supplemented with $MnSO_4$, ampicillin and tryptophan. The seed was grown at 37° C. at 200 rpm for 7 h. Once inoculated the culture was allowed to go its full course before harvesting, relying on tryptophan starvation to switch on the trp promoter late in the cultures exponential phase of growth, when cell densities will be at their highest. Cells were harvested by centrifugation, and the cell paste bagged, flash frozen and stored at -80° C. until extracted. The level of SOD expression obtained from the pilot scale cultures were consistent with those obtained in shake flask experiments. Following purification characterisation of the purified recombinant SOD identified the protein as a dimer, with each subunit having a molecular weight of approximately 21,000 dal and an isoelectric point of 5.5.

From the above results it can be seen that the gene (sod) encoding Bacillus stearothermophilusMn-superoxide dismutase has been cloned in Escherichia coli and its entire nucleotide sequence determined. With the exception of the post-translationally cleaved N-terminal methionine residue, the predicted amino acid sequence exhibits 100% similarity to the previously determined amino acid sequence. The recombinant MnSOD was shown to be functionally active in E. coli, both in vitro and in vivo, and was expressed to 47% of the cells soluble protein by coupling its transcription to the E. coli trp promoter.

EXAMPLE 2

(a) Molecular Cloning of the B. caldotenax sod gene

The oligonucleotide probe utilised to clone the B.caldotenax gene was radiolabelled and used in DNA/DNA hybridisation reactions against B. caldotenax YT1 genomic DNA cleaved with various restriction enzymes. Under the conditions employed (see below) the probe was shown to hybridise strongly to various discrete restriction fragments, including a 4.1 kb HindIII fragment. Accordingly, HindIII-cleaved genomic DNA of approximately this size was isolated from agaorose gels and ligated to HindIII cut pUC19 plasmid DNA. The resultant ligation mixtures were transformed into E.coli TG1 and transformants selected on L-agar containing. ampicillin and XGal. A total of 1100 recombinants (white colonies) were individually screened by in situ colony hybridisation, using the radiolabelled oligonucleotide as a probe. The probe was shown to hybridise strongly to 4 different recombinant clones. Plasmid DNA from one of these clones was isolated and designated pBCM7.

(b) Determination of the B. caldotenax Sod Nucleotide Sequence

In order to localise the position of the sod structural gene within cloned DNA present in pBCM7, plasmid DNA was restricted with various endonucleases and the resultant fragments subjected to Southern blot analysis.

One of the smallest restriction fragments which hybridised to the oligo probe was shown to be a 1.9 kb AccI fragment. This fragment was gel purified from pBCM7 DNA circularised by self-ligation, fragmented by sonication, the staggered ends generated blunt-ended by treatment with T4 polymerase, and gel purified fragments of 500 to 1000 bp inserted into the SmaI site of M13mp8. Template DNA was prepared from 100 of the recombinant clones obtained. The nucleotide sequence data obtained was assembled into one contiguous sequence using the computer software of DNASTAR Inc. The sequence illustrated in FIG. 12 represents a 780 bp portion of the sequence obtained which encompasses the sod structural gene, and was determined on both DNA strands.

Translation of the nucleotide sequence illustrated in FIG. 12 revealed the presence of an ORF of 615 bp beginning with an AUG codon (nt 30) and terminating with a UAA codon (nt 643). Over the region illustrated in FIG. 12 there were 35 nucleotide differences to the equivalent region of the B.stearothermophilus genome. Of these, 21 occurred in the coding region of the gene, resulting in two amino acid differences between the two encoded polypeptides. Thus the BCMnSOD contains Glu and Ile amino acid residues at positions 103 and 188, respectively, whereas the BSMnSOD contains Asp and Val amino acids at the equivalent respective positions. As with the B.stearothermophilus gene, the translational initiation codon-was preceded by a sequence (5'-CAAAAGGAGGAGA-3') (SEQ ID NO: 9) exhibiting strong complimentarity to the 3'-termini of the Bacillus subtilis 16S rRNA (3'-UCUUUCCUCCACU-5') (SEQ ID NO: 10). Similarly, a sequence-exhibiting dyad symmetry occurs immediately 3' to the translational stop codon (nt 654 to 677), and probably represents a Rho-independent transcriptional terminator. In this case, however, the putative RNA stem-loop structure formed would have a higher DG (-26.4 kcal) than the equivalent structure found downstream of the B.stearothermophilus gene ( DG -22.2 kcal) due to a single difference in the nucleotide sequence, viz. a 'T' to 'C' substitution. The sod structural gene exhibits a G+C content of 52.8%, and its codon usage is illustrated in Table 2.

(c) Overexpression of BCMnSOD

To elicit the high expression of the BCMnSOD gene, equivalent plasmids were constructed to those described above. In this case the 1.9 kb AccI fragment was inserted into the AccI site of pMTL1003, to give the recombinant plasmids pBCM8 (see FIG. 13) and pBCM9. In the case of pBCM8 (FIG. 13), sod was orientated such that its expression could be enhanced by transcriptional read-through from the vector trp promoter. Two analogous plasmids pBCM10 (equivalent to pBCM8) and pBCM11 (equivalent to pBCM9) were generated by using pMTL1013 in place of pMTL1003.

Cells harbouring pBCM8 and pBCM9 were grown in complex media (2XYT), supplemented with 100 $\mu$M $MnSO_4$, and transcription from the vector trp promoter induced in late exponential phase by the addition of indole acrylic acid (20 lg/ml). Cells were removed from the cultures at hourly intervals, disrupted by sonication and the SOD activity of the extract determined following removal of cell debris by centrifugation. The levels of expression attained mirrored those observed with the B. stearothermophilus recombinant clones. Thus the maximum level of MnSOD produced by cells carrying pBCM8, 90,710 units per ml of culture (equivalent to 9,913 u/mg soluble protein), was attained after 10 h (FIG. 9). By reference to the specific activity of pure MnSOD (25,000 u/mg), this equated to 40% of the cells soluble protein. Confirmation of these levels was obtained by densiometric scanning of Coomassie blue stained gels following SDS-PAGE of total cell extracts (see FIG. 10). That high expression was due to the vector trp promoter was indicated by the low level of SOD produced (8.9 units per ml of culture) by cells harbouring pBCM9. The ability of E.coli to support high level of expression of the B. caldotenax sod gene was consistent with the observation that its encoding region makes little use of modulator codons (a single CGG and a GGG codon are used), exhibits a codon bias characteristic of highly expressed E.coli genes (Grosjean and Friers, 1982), and is preceded by a near to consensus ribosome binding site.

EXAMPLE 3

Purified, pyrogen-free BS MnSOD was produced from a culture of BS by the following procedure.

After harvesting, cells of BS were broken by high pressure homogenisation and the crude extract batch purified by fractional elution on DE-23 cellulose. The 0.4 m fraction containing MnSOD was chromatographed sequentially as follows:

(i) DEAE-Sepharose by ion exchange gradient chromatography at pH 8.0

(ii) Hydroxylapatite chromatography using phosphate gradient at pH 6.8.

The 30% pure enzyme was depyrogenated and purified to homogeneity by ion exchange gradient chromatography on Q-sepharose at pH 7.5 and by gel filtration on sephaenyl S-200.

Pharmacological Tests (a) Serum Half-life

The half life of BS MnSOD was assessed using a guinea-pig model. The effect of endogenous Cu/ZnSOD interference due to erythrocyte haemolysis was negated by the addition of 5 mM cyanide to the assay system.

A half-life of approximately 6 hours was observed.

(b) Antigenicity

No adverse antigenicity was observed in groups of guinea-pigs (n=12) receiving 1, 2 and 10 mg/kg body weight/6 hrs (4 animals/group) respectively via the intraperitoneal route. Post-mortem investigation of animals sacrificed at 48 and 96 hours respectively (2 animals/dose/time) revealed no deleterious effect on internal organs and gross pathology was normal.

(c) Protective Effect During Cardiac Perfusion

A standard (Ringers) solution for cardiac perfusion was supplemented with 0.1 mg/l of BS MnSOD provided in vials containing 5 mg enzyme, 10 mg lactose and 5$\mu$moles tris HCL.

Six mini-pigs were divided into two groups of 3 animals per group and subjected to procedure which mimicked human open-heart surgery. Specifically, the animals were maintained for 2n hours with clamped aortas while infusing with the test solutions.

At the end of the test period the aortic clamps were removed, normal blood supplies reconnected and standard methods used to restore normal sinus rhythm.

The animals were monitored in the post-operative period and the test animals (those infused with BS MnSOD-containing solutions) exhibited near normal cardiac function, and survived for one month at which time they were sacrificed for pathological examination. No signs of myocardial infarction or other abnormal cardiac tissue pathology was evident.

The animals in the control group exhibited cardiac malfunctions and were all dead after one week.

TABLE I

Bacterial Strains and Plasmid/Phage Vectors

| Strain/plasmid | Relevant Characteristics | Source |
| --- | --- | --- |
| Strains: | | |
| B. stearothermophilus NCA1503 | | |
| B. caldotenax YT1 | | |
| E. coli TG1 | K12 D(lac-pro) supE thi hsdD5/ F'traD36 proA+ B+ lacIQZ M15 | Carter et al., 1985 |
| E. coli W5445 | pro leu thi thr supE44 lacY tonA hsdM hsdR rpsL | Minton et al., 1983 |
| E. coli QC781 | F-, lac-4169 U(sodA::MudIIPR13)23 | D. Touati, Institut Institut Jacques Monod, CNRS Paris, France |
| E. coli QC773 | GC4468 U(sodB-kan) 1-D2 KmR | D. Touati |
| E. coli QC799 | sodA sodB, CmR KmR | D Touati |
| E. coli BMH71-18 mutL | K-12, D(lac-pro) supE thi mutL::Tn10 F'-pro A+ B+ lacIQZ DM15 | Kramer et al., 1984 |
| Plasmids: | | |
| pBR322 | ApR, TcR | Bolivar et al., 1977 |
| pAT153 | ApR, TcR | Twigg & Sherratt, 1980 |
| pUC8/9 | ApR, lacZ' | Vieira & Messing, 1982 |
| pSC101 | TcR, apr | Cohen and Chang, 1978 |
| pKK223-3 | ApR, trp po | Adman & Brosius, 1985 |
| pDR720 | ApR, trp po | Russell & Bennett, 1982 |
| pMTL4 | ApR, | Chamber et al., 1988 |
| pMTL20/23 | ApR, lacZ' | Chambers et al., 1988 |
| pMTL7 | ApR, | This study |
| pMTL8-10 | ApR, par | This study |
| pMTL100 | ApR, par | This study |
| pMTL1013 | ApR, par trp po::lacZ' | This study |
| pMTL1013 | TcR, par trp po::lacZ' | This study |

TABLE I-continued

Bacterial Strains and Plasmid/Phage Vectors

| Strain/plasmid | Relevant Characteristics | Source |
|---|---|---|
| pBCM1 | pAT153 + BSMnSOD, ApR, TcS | This study |
| pBCM2 | pAT153 + BSMnSOD, ApR, TcS | This study |
| pBCM3 | pMTL1003 + BSMnSOD, ApR | This study |
| pBCM4 | pMTL1003 + BSMnSOD, ApR | This study |
| pBCM5 | pMTL1013 + BSMnSOD, TcR | This study |
| pBCM6 | pMTL1013 + BSMnSOD, TcR | This study |
| pBCM7 | pMTLUC19 + BSMnSOD, ApR | This study |
| pBCM8 | pMTL1003 + BSMnSOD, ApR | This study |
| pBCM9 | pMTL1003 + BSMnSOD, ApR | This study |
| pBCM10 | pMTL1013 + BSMnSOD, TcR | This study |
| pBCM11 | pMTl1013 + BSMnSOD, TcR | This study |
| pMTL28 | ApR, lacZ' | This study |
| M13 phage: | | |
| mp8, 18 & 19 | lacZ' | Messing & Vieira, 1982 |
| mtl20 | lacZ' | Chambers et al., 1982 |

TABLE 2

Codon usage of the BSMnSOD and BCMnSOD genes

| | BS | BC | | BS | BC | | BS | BC | | BS | BC |
|---|---|---|---|---|---|---|---|---|---|---|---|
| UUU Phe | 2 | 3 | UCU | 0 | 1 | UAU Tyr | 2 | 2 | UGU Cys | 0 | 0 |
| UUC | 6 | 5 | UCC Ser | 1 | 0 | UAC | 6 | 6 | UGC | 0 | 0 |
| UUA Leu | 0 | 0 | UCA | 0 | 0 | UAA Ter | 1 | 1 | UGA Ter | 0 | 0 |
| UUG | 8 | 9 | UCG | 5 | 5 | UAG | 0 | 0 | UGG Trp | 6 | 6 |
| CUU | 4 | 5 | CCU | 0 | 0 | CAU His | 4 | 4 | CGU | 2 | 2 |
| CUC Leu | 3 | 3 | CCC Pro | 0 | 0 | CAC | 5 | 5 | CGC Arg | 3 | 3 |
| CUA | 0 | 0 | CCA | 3 | 3 | CAA Gln | 3 | 3 | CGA | 0 | 0 |
| CUG | 4 | 2 | CCG | 10 | 10 | CAG | 0 | 0 | CGG | 1 | 1 |
| AUU | 5 | 7 | ACU | 0 | 0 | AAU Asn | 4 | 4 | AGU Ser | 0 | 0 |
| AUC Ile | 4 | 3 | ACC Thr | 1 | 1 | AAC | 13 | 13 | AGC | 5 | 5 |
| AUA | 0 | 0 | ACA | 3 | 2 | AAA Lys | 11 | 10 | AGA Arg | 0 | 0 |
| AUG Met | 3 | 3 | ACG | 7 | 8 | AAG | 1 | 2 | AGG | 0 | 0 |
| GUU | 3 | 2 | GCU | 2 | 1 | GAU Asp | 3 | 2 | GGU | 3 | 4 |
| GUC Val | 2 | 2 | GCC Ala | 4 | 3 | GAC | 5 | 5 | GGC Gly | 11 | 10 |
| GUA | 0 | 0 | GCA | 5 | 5 | GAA Glu | 12 | 12 | GGA | 1 | 0 |
| GUG | 3 | 3 | GCG | 9 | 11 | GAG | 6 | 7 | GGG | 0 | 1 |

Ter - corresponds to translational termination codon.
BC - corresponds to the B. caldotenax gene.
BS - corresponds to the B. stearothermophilus gene.
embolden codons correspond to those codons recognised as modulators of translation in E. coli.

TABLE 3

Levels of Expression of native and recombinant SOD in E. coli.

| Host | Phenotype[a] | Plasmid | SOD specific[b] activity (U/mg) |
|---|---|---|---|
| TG1 | A+, B+ | — | 55.5 |
| QC781 | A−, B+ | — | 36 |
| QC773 | A+, B− | — | 1.9 |
| QC799 | A−, B− | — | 1.6 |
| TG1 | A+, B+ | pBCM3 | 12,000 |
| QC781 | A−, B+ | " | 12,000 |
| QC773 | A+, B− | " | 5,000 |
| QC799 | A−, B− | " | 4,000 |
| TG1 | A+, B+ | pBCM8 | 9,913 |
| QC781 | A−, B+ | " | 3,650 |
| QC773 | A+, B− | " | 2,581 |
| QC799 | A−, B− | " | 1,944 |

[a]Phenotypes A and B refer to the sodA and sodB gene, respectively, + or − indicating whether the gene is functional (+) or defective (−).
[b]The levels of sod expression directed by pBCM3/8 in a range of E. coli hosts, exhibiting varying degrees of native SOD activity, were estimated by assaying SOD levels in cell extracts (Table 3). In this case transcription froj the trp promoter was induced late in their exponential phase following tryptophan depletion from the media (2XYT).

We claim:

1. A pharmaceutical composition for use in the prophylaxis or treatment of pathological conditions resulting from the presence of superoxide radicals, comprising a Manganese-superoxide dismutase (MnSOD) enzyme and a pharmaceutically acceptable excipient, the MnSOD enzyme (a) being in native form, (b) having essentially the amino acid sequence of SEQ ID NO: 17 or SEQ ID NO:29, (c) being free of pyrogens consisting of macromolecular substances native to *Bacillus stearothermophilus* (BS) or *Bacillus caldotenax* (BC) and (d) catalysing dismutation of $O_2^-$ to $H_2O_2$.

2. A pharmaceutical composition according to claim 1 wherein the MnSOD enzyme is obtained in native form by (a) culturing an MnSOD enzyme-producing microorganism so as to produce an MnSOD enzyme-containing culture,(b) isolating MnSOD enzyme from the culture, and (c) purifying the isolated MnSOD enzyme so as to produce purified enzyme which is essentially unmodified, chemically, compared to the MnSOD enzyme present in the MnSOD-containing culture produced in step (a).

3. A pharmaceutical composition according to claim 1 wherein said MnSOD enzyme is produced by culturing a transformed microorganism of a species other than *B stearothermophllus* or *B caldotenax*.

4. A pharmaceutical composition according to claim 1 wherein said MnSOD enzyme has an amino acid sequence selected from the group consisting of:
   (i) SEQ ID NO: 17, and
   (ii) SEQ ID NO: 29,
said enzyme having the properties of:
   (a) catalyzing dismutation of $O_2^-$ to $H_2O_2$, and
   (b) inducing no antigenic reaction in a guinea-pig 96 hours following intra-peritoneal administration to said guinea pig of 10 mg enzyme per kg body weight of said guinea pig.

5. A pharmaceutical composition according to claim 1 in the form of an injectable solution or a solution for perfusing tissues during surgical or transplantation procedures.

6. A pharmaceutical composition according to claim 5 containing from 0.01 to 1.0 mg/l of said MnSOD enzyme.

7. A process for producing a pharmaceutical composition which comprises the steps of (a) culturing a Manganese-superoxide dismutase (MnSOD) enzyme-producing microorganism so as to produce an MnSOD enzyme-containing culture, (b) isolating MnSOD enzyme from the culture, (c) purifying the isolated MnSOD enzyme so as to produce purified enzyme which is free of pyrogen derived from *Bacillus stearothermophilus* and free of pyrogen derived from *Bacillus caldotenax* and is essentially unmodified, chemically, compared to the MnSOD enzyme present in the MnSOD-containing culture produced in step (a), and (d) mixing the chemically unmodified MnSOD enzyme with a pharmaceutically acceptable excipient, wherein said MnSOD enzyme has essentially the amino acid sequence of SEQ ID NO: 17 or SEQ ID NO: 29 and catalyses dismutation of $O_2^-$ to $H_2O_2$.

8. The process of claim 7 wherein purification of said isolated MnSOD enzyme in step (c) is effected by a procedure comprising the steps of:
   (i) subjecting said isolated enzyme to ion exchange gradient chromatography on Q-sepharose at about pH 7.5, and
   (ii) subjecting said isolated enzyme to gel filtration on sephacryl S-200.

9. The process of claim 8 wherein said purification procedure additionally comprises the steps of subjecting said isolated enzyme to:
   (i) ion exchange gradient chromatography on DEAE-Sepharose at about pH 8.0; and
   (ii) phosphate gradient chromatography on hydroxylaptite at about pH 6.8.

10. A pharmaceutical composition produced by the process of claim 8.

11. A method for the prophylaxis of pathological conditions resulting from the presence of superoxide radicals, which comprises administering to a patient in need of such prophylaxis an effective amount of a Manganese-superoxide dismutase (MnSOD) enzyme, wherein the MnSOD enzyme is in native form, has essentially the amino acid sequence of SEQ ID NO: 17 or SEQ ID NO: 29, is free of pyrogen and catalyses dismutation of $O_2^-$ to $H_2O_2$.

12. A manganese-superoxide dismutase enzyme in substantially pure form and having the amino acid sequence of:
   SEQ ID NO: 29,
said enzyme having the properties of:
   (a) catalyzing dismutation of $O_2^-$ to $H_2O_2$, and
   (b) inducing no antigenic reaction in a guinea-pig 96 hours following intra-peritoneal administration to said guinea pig of 10 mg enzyme per kg body weight of said guinea pig.

* * * * *

SEQUENCE LISTING ( 1 ) GENERAL INFORMATION:

( i i i ) NUMBER OF SEQUENCES: 29

( 2 ) INFORMATION FOR SEQ ID NO: 1:

( i ) SEQUENCE CHARACTERISTICS:
        ( A ) LENGTH: 29 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Escherichia coli ( x i ) SEQUENCE DESCRIPTION: SEQ ID NO: 1:

TTGACAATTA ATCATCGAAC TAGTTAACT        29

( 2 ) INFORMATION FOR SEQ ID NO: 2:

( i ) SEQUENCE CHARACTERISTICS:
        ( A ) LENGTH: 6 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO: 2:

TTGACA        6

( 2 ) INFORMATION FOR SEQ ID NO: 3:

( i ) SEQUENCE CHARACTERISTICS:
        ( A ) LENGTH: 6 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO: 3:

TTAACT        6

( 2 ) INFORMATION FOR SEQ ID NO: 4:

( i ) SEQUENCE CHARACTERISTICS:
        ( A ) LENGTH: 6 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO: 4:

TCAATT        6

( 2 ) INFORMATION FOR SEQ ID NO: 5:

( i ) SEQUENCE CHARACTERISTICS:
        ( A ) LENGTH: 6 base pairs
        ( B ) TYPE: nucleic acid (C) STRANDEDNESS: double
            (D) TOPOLOGY: linear (ii) MOLECULE TYPE: DNA (genomic)

(xi) SEQUENCE DESCRIPTION: SEQ ID NO: 5:

ACAGTT                                                                                                              6

(2) INFORMATION FOR SEQ ID NO: 6:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 6:

ATTAATCATC GAACTAG                                                                                                 17

(2) INFORMATION FOR SEQ ID NO: 7:

(i) SEQUENCE CHARACTERISTICS:
            (A) LENGTH: 33 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 7:

GCTTACTCCC CATCCCCCCA GTGAATTCCC CTG                                                                                33

(2) INFORMATION FOR SEQ ID NO: 8:

(i) SEQUENCE CHARACTERISTICS:
            (A) LENGTH: 15 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 8:

AGTACGCAGC TTGGC                                                                                                   15

(2) INFORMATION FOR SEQ ID NO: 9:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: NO (vi) ORIGINAL SOURCE:
            (A) ORGANISM: Bacillus stearothermophilus (xi) SEQUENCE DESCRIPTION: SEQ ID NO: 9:

CAAAAGGAGG AGA                                                                                                     13

(2) INFORMATION FOR SEQ ID NO: 10:

(i) SEQUENCE CHARACTERISTICS:

(A) LENGTH: 13 base pairs
(B) TYPE: nucleic acid
(C) STRANDEDNESS: single
(D) TOPOLOGY: linear (ii) MOLECULE TYPE: rRNA (iii) HYPOTHETICAL: NO (iii) ANTI-SENSE: NO (vi) ORIGINAL SOURCE:
(A) ORGANISM: Bacillus subtilis (xi) SEQUENCE DESCRIPTION: SEQ ID NO: 10:

UCUUUCCUCC ACU                                                                                              13

(2) INFORMATION FOR SEQ ID NO: 11:

(i) SEQUENCE CHARACTERISTICS:
(A) LENGTH: 44 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 11:

TCGAGATCTC CCGGGATCCG ATATCTGATC AGTTAACAGA TCTG                                                             44

(2) INFORMATION FOR SEQ ID NO: 12:

(i) SEQUENCE CHARACTERISTICS:
(A) LENGTH: 44 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 12:

AATTCAGATC TGTTAACTGA TCAGATATCG GATCCCGGGA GATC                                                             44

(2) INFORMATION FOR SEQ ID NO: 13:

(i) SEQUENCE CHARACTERISTICS:
(A) LENGTH: 50 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO: 13:

CACATCGACA AAGAAACGAT GAACATTCAC CACACGAAGC ACCATAACAC                                                       50

(2) INFORMATION FOR SEQ ID NO: 14:

(i) SEQUENCE CHARACTERISTICS:
(A) LENGTH: 17 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 14:

His Ile Asp Lys Glu Thr Met Asn Ile His His Thr Lys His His Asn
1               5                   10                  15

Thr ( 2 ) INFORMATION FOR SEQ ID NO: 15:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 15:

```
GTGTAGCTGT  TTCTTTGCTA  CTTGTAGGTG  GTGTGCTTTG  TGGTGTTGTG              50
```

( 2 ) INFORMATION FOR SEQ ID NO: 16:

( i ) SEQUENCE CHARACTERISTICS:
        ( A ) LENGTH: 1294 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 387..1001

( x i ) SEQUENCE DESCRIPTION: SEQ ID NO: 16:

```
AAGCTTTTCC  ACAGCTGGAC  GAATACGTTC  ATCGCAGACA  CACCTTTCTT  TATCTCCTTT     60

TCCATTGTAG  CCGGGAAAGA  GGAAGAATTC  AACTTGAGAC  AAAGAAAAAG  CGGGCATCTT    120

CCCGCTTTAG  TCAGAAGGCA  AATGAAAGGT  TTCAAGCAAG  GCGCGCCATT  GCAACACCCG    180

TTCATTTAGT  GCATCGGCTT  CGGAACGAAT  GGCAGCCATA  TACTATAGCT  TGTCATTATG    240

AAGAAACGGT  CAACGGTGTG  TTGAAAATAT  GTAAACAAAA  ACCGAGGACA  AGCAAGTCGA    300

TTGAAACATT  GTGCCAAGTT  TGGTAAGCTA  ATCTCAAGCG  AACGCTTTGG  CGTTCGTGTA    360

CATAAATCAA  AAAGGAGGAG  ATCGGT ATG  CCA TTT GAA TTG CCA GCA TTG CCG       413
                              Met Pro Phe Glu Leu Pro Ala Leu Pro
                               1               5

TAT CCG TAT GAT GCT CTG GAG CCG CAC ATC GAC AAA GAA ACG ATG AAC          461
Tyr Pro Tyr Asp Ala Leu Glu Pro His Ile Asp Lys Glu Thr Met Asn
 10              15                  20                  25

ATT CAC CAC ACG AAG CAC CAT AAC ACA TAC GTT ACA AAT TTG AAT GCG          509
Ile His His Thr Lys His His Asn Thr Tyr Val Thr Asn Leu Asn Ala
                 30                  35                  40

GCG CTT GAA GGA CAT CCG GAT TTG CAA AAC AAA TCG CTC GAA GAA CTG          557
Ala Leu Glu Gly His Pro Asp Leu Gln Asn Lys Ser Leu Glu Glu Leu
             45                  50                  55

CTC AGC AAT TTG GAA GCC CTT CCG GAA AGC ATC CGC ACG GCG GTG CGC          605
Leu Ser Asn Leu Glu Ala Leu Pro Glu Ser Ile Arg Thr Ala Val Arg
         60                  65                  70

AAC AAC GGC GGC GGC CAT GCG AAC CAC TCG CTT TTC TGG ACG ATT TTG          653
Asn Asn Gly Gly Gly His Ala Asn His Ser Leu Phe Trp Thr Ile Leu
     75                  80                  85

TCG CCA AAT GGC GGC GGC GAG CCG ACG GGT GAG CTG GCT GAC GCC ATC          701
Ser Pro Asn Gly Gly Gly Glu Pro Thr Gly Glu Leu Ala Asp Ala Ile
 90                  95                 100                 105

AAC AAA AAA TTC GGC AGC TTC ACC GCG TTC AAA GAC GAG TTT TCG AAA          749
Asn Lys Lys Phe Gly Ser Phe Thr Ala Phe Lys Asp Glu Phe Ser Lys
                110                 115                 120

GCA GCG GCC GGC CGT TTC GGT TCC GGT TGG GCA TGG CTT GTT GTG AAC          797
Ala Ala Ala Gly Arg Phe Gly Ser Gly Trp Ala Trp Leu Val Val Asn
            125                 130                 135
```

```
AAC  GGC  GAG  CTG  GAA  ATC  ACA  AGC  ACG  CCG  AAC  CAA  GAT  TCG  CCG  ATT        845
Asn  Gly  Glu  Leu  Glu  Ile  Thr  Ser  Thr  Pro  Asn  Gln  Asp  Ser  Pro  Ile
          140                 145                     150

ATG  GAA  GGC  AAA  ACG  CCG  ATT  CTC  GGC  TTG  GAC  GTT  TGG  GAG  CAT  CGC        893
Met  Glu  Gly  Lys  Thr  Pro  Ile  Leu  Gly  Leu  Asp  Val  Trp  Glu  His  Arg
155                      160                     165

TAC  TAC  TTG  AAA  TAC  CAA  AAC  CGC  CGT  CCG  GAA  TAC  ATT  GCC  GCA  TTC        941
Tyr  Tyr  Leu  Lys  Tyr  Gln  Asn  Arg  Arg  Pro  Glu  Tyr  Ile  Ala  Ala  Phe
170                      175                     180                      185

TGG  AAC  GTC  GTC  AAC  TGG  GAC  GAA  GTG  GCG  AAA  CGG  TAC  AGC  GAA  GCG        989
Trp  Asn  Val  Val  Asn  Trp  Asp  Glu  Val  Ala  Lys  Arg  Tyr  Ser  Glu  Ala
               190                      195                          200

AAA  GCA  AAA  TAATGAACAA  AGCGGGGCGA  AACACAACGC  TCCGCTTTTT                         1038
Lys  Ala  Lys
          205

TTTCGACGAA  GGGGGCAGGC  AAAGGGAGCG  GTTTTCGTTG  CGCCGGGTGC  ATAGAGGCGG                1098

CAGAAATGGC  CACACTACCC  GATAGATGAA  AAGGGAGTT   TGCAATGGCA  TTTTTCCAAA                1158

AACTAACCGG  CCAAGAACAA  GTGAACCGCG  ACCTGTTGCT  TTTGCTTTGC  ATCGGCGGGT                1218

TTTACGCGCT  CGGTGTTTCC  CTGTCGAACA  CGTTTGTCAA  CATTTATTTG  TGGAAACAGA                1278

CCGGCGATTT  TCGCGA                                                                    1294
```

( 2 ) INFORMATION FOR SEQ ID NO: 17:

( i ) SEQUENCE CHARACTERISTICS:
        ( A ) LENGTH: 204 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 17:

```
Met  Pro  Phe  Glu  Leu  Pro  Ala  Leu  Pro  Tyr  Pro  Tyr  Asp  Ala  Leu  Glu
 1              5                        10                       15

Pro  His  Ile  Asp  Lys  Glu  Thr  Met  Asn  Ile  His  His  Thr  Lys  His  His
               20                      25                       30

Asn  Thr  Tyr  Val  Thr  Asn  Leu  Asn  Ala  Ala  Leu  Glu  Gly  His  Pro  Asp
               35                      40                       45

Leu  Gln  Asn  Lys  Ser  Leu  Glu  Glu  Leu  Leu  Ser  Asn  Leu  Glu  Ala  Leu
          50                       55                       60

Pro  Glu  Ser  Ile  Arg  Thr  Ala  Val  Arg  Asn  Asn  Gly  Gly  Gly  His  Ala
65                       70                       75                       80

Asn  His  Ser  Leu  Phe  Trp  Thr  Ile  Leu  Ser  Pro  Asn  Gly  Gly  Gly  Glu
               85                      90                       95

Pro  Thr  Gly  Glu  Leu  Ala  Asp  Ala  Ile  Asn  Lys  Lys  Phe  Gly  Ser  Phe
               100                     105                      110

Thr  Ala  Phe  Lys  Asp  Glu  Phe  Ser  Lys  Ala  Ala  Ala  Gly  Arg  Phe  Gly
               115                     120                      125

Ser  Gly  Trp  Ala  Trp  Leu  Val  Val  Asn  Asn  Gly  Glu  Leu  Glu  Ile  Thr
               130                     135                      140

Ser  Thr  Pro  Asn  Gln  Asp  Ser  Pro  Ile  Met  Glu  Gly  Lys  Thr  Pro  Ile
145                      150                     155                      160

Leu  Gly  Leu  Asp  Val  Trp  Glu  His  Ala  Tyr  Tyr  Leu  Lys  Tyr  Gln  Asn
                    165                     170                      175

Arg  Arg  Pro  Glu  Tyr  Ile  Ala  Ala  Phe  Trp  Asn  Val  Val  Asn  Trp  Asp
               180                     185                      190

Glu  Val  Ala  Lys  Arg  Tyr  Ser  Glu  Ala  Lys  Ala  Lys
```

(2) INFORMATION FOR SEQ ID NO: 18:

(i) SEQUENCE CHARACTERISTICS:
       (A) LENGTH: 51 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 18:

```
Met Ala Phe Phe Gln Lys Leu Thr Gly Gln Glu Gln Val Asn Arg Asp
1               5                   10                  15

Leu Leu Leu Leu Leu Cys Ile Gly Gly Phe Tyr Ala Leu Gly Val Ser
                20              25                  30

Leu Ser Asn Thr Phe Val Asn Ile Tyr Leu Trp Lys Gln Thr Gly Asp
            35              40              45

Phe Arg Glu
50
```

(2) INFORMATION FOR SEQ ID NO: 19:

(i) SEQUENCE CHARACTERISTICS:
       (A) LENGTH: 108 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO: 19:

```
ATGACCATGA TTACGAATTC GAGCTCGGTA CCCGGGGATC CTCTAGAGTC GACGTCACGC      60
GTCCATGGAG ATCTCGAGGC CTGCAGGCAT GCAAGCTTGG CACTGGCC                  108
```

(2) INFORMATION FOR SEQ ID NO: 20:

(i) SEQUENCE CHARACTERISTICS:
       (A) LENGTH: 108 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO: 20:

```
ATGACCATGA TTACGCCAAG CTTGCATGCG TGCAGGCCTC GAGATCTCCA TGGACGCGTG      60
ACGTCGACTC TAGAGGATCC CCGGGTACCG AGCTCGAATT CACTGGCC                  108
```

(2) INFORMATION FOR SEQ ID NO: 21:

(i) SEQUENCE CHARACTERISTICS:
       (A) LENGTH: 138 base pairs
       (B) TYPE: nucleic acid
       (C) STRANDEDNESS: double
       (D) TOPOLOGY: linear (ii) MOLECULE TYPE: DNA (genomic)

(ix) FEATURE:
       (A) NAME/KEY: CDS
       (B) LOCATION: 1..15

(xi) SEQUENCE DESCRIPTION: SEQ ID NO: 21:

```
ATG ACC ATG ATT ACG AATTGCCGGC GATATCGGAT CCATATGACG TCGACGCGTC       55
Met Thr Met Ile Thr
```

TGCAGAAGCT TCTAGAATTC GAGCTCCCGG GTACCATGGC ATGCATCGAT AGATCTCGAG    115

GCCTCGCGAG CTTGGCACTG GCC    138

( 2 ) INFORMATION FOR SEQ ID NO: 22:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 22:

Met Thr Met Ile Thr
1               5

( 2 ) INFORMATION FOR SEQ ID NO: 23:

( i ) SEQUENCE CHARACTERISTICS:
        ( A ) LENGTH: 138 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO: 23:

ATGACCATGA TTACGCCAAG CTCGCGAGGC CTCGAGATCT ATCGATGCAT GCCATGGTAC    60

CCGGGAGCTC GAATTCTAGA AGCTTCTGCA GACGCGTCGA CGTCATATGG ATCCGATATC    120

GCCGGCAATT CACTGGCC    138

( 2 ) INFORMATION FOR SEQ ID NO: 24:

( i ) SEQUENCE CHARACTERISTICS:
        ( A ) LENGTH: 155 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO: 24:

ATGACCATGA TTACGCCAAG GAGCTCGGTA CCCCGGGATC CTCAGAGTCG ACGTCACGCG    60

TCCATGGAGA TCTCGAGGCC TGCAGGCATG CAAGCTTGCA TGCCTGCAGG TCGACTCTAG    120

AGGATCCCCG GGTACCGAGC TCGAATTCAC TGGCC    155

( 2 ) INFORMATION FOR SEQ ID NO: 25:

( i ) SEQUENCE CHARACTERISTICS:
        ( A ) LENGTH: 162 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO: 25:

ATGACCATGA TTACGCCAAG CTTGCATGCC TGCAGGCCTC GAGATCTCCA TGGACGCGTG    60

ACGTCGACTC TAGAGGATCC CCGGGTACCG AGCTCGAATT CGAGCTCGGT ACCCGGGGAT    120

CCTCTAGAGT CGACCTGCAG GCATGCAAGC TTGGCACTGG CC    162

( 2 ) INFORMATION FOR SEQ ID NO: 26:

( i ) SEQUENCE CHARACTERISTICS:
  ( A ) LENGTH: 138 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO: 26:

| | | | | | |
|---|---|---|---|---|---|
| ATGACCATGA | TTACGAATTC | TAGAAGCTTC | TGCAGACGCG | TCGACGTCAT | ATGGATCCGA | 60 |
| TATCGCCGGC | AATTCGAGCT | CCCGGGTACC | ATGGCATGCA | TCGATAGATC | TCGAGGCCTC | 120 |
| GCGAGCTTGG | CACTGGCC | | | | | 138 |

( 2 ) INFORMATION FOR SEQ ID NO: 27:

( i ) SEQUENCE CHARACTERISTICS:
    ( A ) LENGTH: 142 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO: 27:

| | | | | | |
|---|---|---|---|---|---|
| ATGACCATGA | TTACGCCAAG | CTCGCGAGGC | CTCGAGATCT | CCCGGGATCC | GATATCTGAT | 60 |
| CAGTTAACAG | ATCTGAATTC | TAGAAGCTTC | TGCAGACGCG | TCGACGTCAT | ATGGATCCGA | 120 |
| TATCGCCGGC | AATTCACTGG | CC | | | | 142 |

( 2 ) INFORMATION FOR SEQ ID NO: 28:

( i ) SEQUENCE CHARACTERISTICS:
    ( A ) LENGTH: 780 base pairs
    ( B ) TYPE: nucleic acid
    ( C ) STRANDEDNESS: double
    ( D ) TOPOLOGY: linear ( i i ) MOLECULE TYPE: DNA (genomic)

( i x ) FEATURE:
    ( A ) NAME/KEY: CDS
    ( B ) LOCATION: 31..645

( x i ) SEQUENCE DESCRIPTION: SEQ ID NO: 28:

```
TGTACATAAA  TCAAAAGGA  GGAGATCGGT  ATG  CCA  TTT  GAA  TTG  CCA  GCA  TTG         54
                                  Met  Pro  Phe  Glu  Leu  Pro  Ala  Leu
                                   1                 5

CCG  TAT  CCG  TAT  GAT  GCG  CTT  GAG  CCG  CAC  ATC  GAC  AAA  GAA  ACG  ATG   102
Pro  Tyr  Pro  Tyr  Asp  Ala  Leu  Glu  Pro  His  Ile  Asp  Lys  Glu  Thr  Met
          10                 15                 20

AAC  ATT  CAC  CAC  ACG  AAG  CAC  CAT  AAC  ACA  TAC  GTT  ACA  AAT  TTG  AAT   150
Asn  Ile  His  His  Thr  Lys  His  His  Asn  Thr  Tyr  Val  Thr  Asn  Leu  Asn
 25                 30                 35                             40

GCG  GCG  CTT  GAA  GGG  CAT  CCG  GAT  TTG  CAA  AAC  AAA  TCG  CTC  GAA  GAA   198
Ala  Ala  Leu  Glu  Gly  His  Pro  Asp  Leu  Gln  Asn  Lys  Ser  Leu  Glu  Glu
                     45                 50                             55

TTG  CTC  AGC  AAT  TTG  GAA  GCC  CTT  CCG  GAA  AGC  ATT  CGC  ACG  GCG  GTG   246
Leu  Leu  Ser  Asn  Leu  Glu  Ala  Leu  Pro  Glu  Ser  Ile  Arg  Thr  Ala  Val
               60                 65                             70

CGC  AAC  AAC  GGC  GGC  GGT  CAT  GCA  AAC  CAC  TCG  CTT  TTC  TGG  ACG  ATT   294
Arg  Asn  Asn  Gly  Gly  Gly  His  Ala  Asn  His  Ser  Leu  Phe  Trp  Thr  Ile
          75                 80                 85

TTG  TCG  CCA  AAT  GGC  GGC  GGT  GAG  CCG  ACG  GGT  GAG  CTG  GCT  GAG  GCG   342
Leu  Ser  Pro  Asn  Gly  Gly  Gly  Glu  Pro  Thr  Gly  Glu  Leu  Ala  Glu  Ala
     90                 95                      100
```

```
ATC  AAC  AAA  AAA  TTC  GGC  AGC  TTC  ACC  GCG  TTT  AAA  GAC  GAG  TTT  TCG       390
Ile  Asn  Lys  Lys  Phe  Gly  Ser  Phe  Thr  Ala  Phe  Lys  Asp  Glu  Phe  Ser
105            110                      115                           120

AAA  GCA  GCG  GCC  GGC  CGT  TTC  GGT  TCT  GGC  TGG  GCA  TGG  CTT  GTC  GTG       438
Lys  Ala  Ala  Ala  Gly  Arg  Phe  Gly  Ser  Gly  Trp  Ala  Trp  Leu  Val  Val
                    125                      130                      135

AAC  AAC  GGC  GAG  CTG  GAA  ATT  ACG  AGC  ACG  CCG  AAC  CAA  GAC  TCG  CCG       486
Asn  Asn  Gly  Glu  Leu  Glu  Ile  Thr  Ser  Thr  Pro  Asn  Gln  Asp  Ser  Pro
               140                      145                      150

ATC  ATG  GAA  GGC  AAA  ACG  CCG  ATT  CTC  GGC  TTG  GAC  GTT  TGG  GAG  CAT       534
Ile  Met  Glu  Gly  Lys  Thr  Pro  Ile  Leu  Gly  Leu  Asp  Val  Trp  Glu  His
          155                      160                      165

GCG  TAC  TAC  TTG  CCC  TAC  CAA  AAC  CGC  CGT  CCG  GAA  TAC  ATT  GCC  GCA       582
Ala  Tyr  Tyr  Leu  Lys  Tyr  Gln  Asn  Arg  Arg  Pro  Glu  Tyr  Ile  Ala  Ala
     170                      175                      180

TTC  TGG  AAC  ATT  GTC  AAC  TGG  GAC  GAA  GTG  GCG  AAA  CGG  TAC  AGC  GAA       630
Phe  Trp  Asn  Ile  Val  Asn  Trp  Asp  Glu  Val  Ala  Lys  Arg  Tyr  Ser  Glu
185                      190                      195                      200

GCG  AAA  GCG  AAG  TAATCAACAA  AGCGGGGCGA  AACAAAACGC  CCCGCTTTTT                    682
Ala  Lys  Ala  Lys
               205

TTAGCGACGG  AGGGTGCAGG  CAAAGGAAGC  GGTTTTCTTC  GCGCCGGGTG  CATAGAGGCT                742

GCGGAAATGG  CCACACTACC  GGATAGATGA  AAAGGGGA                                          780
```

( 2 ) INFORMATION FOR SEQ ID NO: 29:

( i ) SEQUENCE CHARACTERISTICS:
        ( A ) LENGTH: 204 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 29:

```
Met  Pro  Phe  Glu  Leu  Pro  Ala  Leu  Pro  Tyr  Pro  Tyr  Asp  Ala  Leu  Glu
1              5                        10                      15

Pro  His  Ile  Asp  Lys  Glu  Thr  Met  Asn  Ile  His  His  Thr  Lys  His  His
               20                       25                      30

Asn  Thr  Tyr  Val  Thr  Asn  Leu  Asn  Ala  Ala  Leu  Glu  Gly  His  Pro  Asp
          35                       40                      45

Leu  Gln  Asn  Lys  Ser  Leu  Glu  Glu  Leu  Leu  Ser  Asn  Leu  Glu  Ala  Leu
     50                       55                      60

Pro  Glu  Ser  Ile  Arg  Thr  Ala  Val  Arg  Asn  Asn  Gly  Gly  Gly  His  Ala
65                       70                      75                      80

Asn  His  Ser  Leu  Phe  Trp  Thr  Ile  Leu  Ser  Pro  Asn  Gly  Gly  Gly  Glu
               85                       90                      95

Pro  Thr  Gly  Glu  Leu  Ala  Glu  Ala  Ile  Asn  Lys  Lys  Phe  Gly  Ser  Phe
          100                      105                     110

Thr  Ala  Phe  Lys  Asp  Glu  Phe  Ser  Lys  Ala  Ala  Ala  Gly  Arg  Phe  Gly
     115                      120                     125

Ser  Gly  Trp  Ala  Trp  Leu  Val  Val  Asn  Asn  Gly  Glu  Leu  Glu  Ile  Thr
130                      135                     140

Ser  Thr  Pro  Asn  Gln  Asp  Ser  Pro  Ile  Met  Glu  Gly  Lys  Thr  Pro  Ile
145                      150                     155                     160

Leu  Gly  Leu  Asp  Val  Trp  Glu  His  Ala  Tyr  Tyr  Leu  Lys  Tyr  Gln  Asn
               165                      170                     175

Arg  Arg  Pro  Glu  Tyr  Ile  Ala  Ala  Phe  Trp  Asn  Ile  Val  Asn  Trp  Asp
          180                      185                     190
```

Glu Val Ala Lys Arg Tyr Ser Glu Ala Lys Ala Lys
       195                     200